United States Patent
Ish-Yamini Tomer et al.

(10) Patent No.: US 8,896,211 B2
(45) Date of Patent: Nov. 25, 2014

(54) PHYSICAL MEANS AND METHODS FOR INDUCING REGENERATIVE EFFECTS ON LIVING TISSUES AND FLUIDS

(71) Applicant: OrTeron (T.O) Ltd, Kfar Saba (IL)

(72) Inventors: Orit Ish-Yamini Tomer, Netanya (IL); Tamar Levin, Kfar Saba (IL)

(73) Assignee: OrTeron (T.O) Ltd, Kfar Saba (IL)

( * ) Notice: Subject to any disclaimer, the term of this patent is extended or adjusted under 35 U.S.C. 154(b) by 0 days.

(21) Appl. No.: 13/874,547

(22) Filed: May 1, 2013

(65) Prior Publication Data
US 2014/0199756 A1 Jul. 17, 2014

Related U.S. Application Data

(60) Provisional application No. 61/753,022, filed on Jan. 16, 2013.

(51) Int. Cl.
H01J 7/24 (2006.01)
H05B 31/26 (2006.01)
(Continued)

(52) U.S. Cl.
CPC .......... *A61B 18/042* (2013.01); *H05H 2240/20* (2013.01); *H01J 37/32669* (2013.01);
(Continued)

(58) Field of Classification Search
CPC ............... H01J 37/32009; H01J 37/32018; H01J 37/32027; H01J 37/32036; H01J 37/32055; H01J 37/32073; H01J 37/32082; H01J 37/32137; H01J 37/32146; H01J 37/32155; H01J 37/32321; H01J 37/32348; H01J 37/32623; H01J 37/32642; H01J 37/32651; H01J 37/3266; H01J 37/32669; A61M 2202/02; A61L 2/14; A61L 33/0094; A61L 2400/18; A61F 2013/51069; A61B 18/042; A61B 2018/00583
USPC ............... 604/20, 23–25; 606/40–41; 607/99; 210/198.1, 748.17; 315/111.21, 315/111.31, 111.41, 111.51, 111.61, 315/111.71; 47/1.01 R
See application file for complete search history.

(56) References Cited

U.S. PATENT DOCUMENTS 4,739,169 A * 4/1988 Kurosawa et al. ......... 250/423 R
4,978,346 A * 12/1990 Bentley .......................... 606/27
(Continued)

FOREIGN PATENT DOCUMENTS

WO 2005084569 A1 9/2005
WO 2008131407 A1 10/2008
WO 2012003348 A2 1/2012

OTHER PUBLICATIONS

International Search Report and Written Opinion dated May 26, 2014 from European Patent Office in co-pending International Application No. PCT/IL2014/050053.

*Primary Examiner* — Andrew Gilbert
(74) *Attorney, Agent, or Firm* — The Law Office of Michael E. Kondoudis

(57) ABSTRACT

The present invention discloses a system for the administration of a plasma modified field (PMF) to a subject comprising: (a) a non thermal plasma (NTP) emitting source for emitting a plasma beam; (b) a plasma modified field coupling mechanism (PMFCM) comprising a plasma beam dish having at least one opening for the passage of said plasma beam; said plasma beam dish having a first surface and a second opposite surface; and (c) a controller for controlling said PMFCM. In a main aspect of the invention, said first surface of said plasma beam dish is mounted with: (i) at least one coupling element selected from the group consisting of: (1) at least one ferroelectric element for providing said field; (2) at least one ferromagnetic element for providing said field; (3) at least one piezoelectric element for providing said field; and (4) at least one piezomagnetic element for providing said field; and (ii) at least one reflecting element. In a further main aspect, the PMFCM and said controller are configured to adjust any of said at least one coupling and reflecting element in a predetermined manner thereby providing said PMF for inducing a therapeutic or regenerative or beneficial effect on said subject. The present invention further discloses methods and use of the aforementioned system.

2 Claims, 9 Drawing Sheets

(51) Int. Cl.
  *A61M 37/00* (2006.01)
  *A61B 18/04* (2006.01)
  *H01J 37/32* (2006.01)
  *B09C 1/00* (2006.01)
  *A01G 7/04* (2006.01)
  *H05H 1/24* (2006.01)

(52) U.S. Cl.
  CPC ... *B09C 1/00* (2013.01); *A01G 7/04* (2013.01); *H05H 1/24* (2013.01)
  USPC .................................. 315/111.21; 604/23

(56) References Cited

U.S. PATENT DOCUMENTS

| | | | |
|---|---|---|---|
| 5,081,398 A * | 1/1992 | Asmussen et al. | 315/111.41 |
| 5,189,446 A * | 2/1993 | Barnes et al. | 315/111.41 |
| 5,562,952 A * | 10/1996 | Nakahigashi et al. | 427/534 |
| 5,895,558 A * | 4/1999 | Spence | 204/164 |
| 6,099,523 A * | 8/2000 | Kim et al. | 606/40 |
| 6,387,088 B1 * | 5/2002 | Shattuck et al. | 606/2 |
| 6,911,779 B2 * | 6/2005 | Madocks | 315/111.21 |
| 7,220,261 B2 * | 5/2007 | Truckai et al. | 606/41 |
| 7,323,821 B2 * | 1/2008 | Schwarzl et al. | 315/111.41 |
| 7,493,969 B2 * | 2/2009 | Burnett et al. | 175/88 |
| 2001/0034519 A1 * | 10/2001 | Goble et al. | 606/41 |
| 2002/0161362 A1 | 10/2002 | Penny et al. | |
| 2003/0103877 A1 * | 6/2003 | Long | 422/186.04 |
| 2003/0125727 A1 * | 7/2003 | Truckai et al. | 606/41 |
| 2006/0189976 A1 * | 8/2006 | Karni et al. | 606/41 |
| 2008/0017616 A1 * | 1/2008 | Lee et al. | 219/121.48 |
| 2009/0012589 A1 * | 1/2009 | Watson | 607/99 |
| 2010/0130911 A1 | 5/2010 | Morfill et al. | |
| 2010/0145253 A1 | 6/2010 | Gutsol et al. | |
| 2010/0296977 A1 * | 11/2010 | Hancock | 422/186 |
| 2013/0026919 A1 * | 1/2013 | Rosener | 315/111.41 |
| 2013/0072859 A1 * | 3/2013 | Watson et al. | 604/23 |
| 2013/0345620 A1 * | 12/2013 | Zemel et al. | 604/24 |
| 2014/0074090 A1 * | 3/2014 | Lam et al. | 606/49 |

* cited by examiner

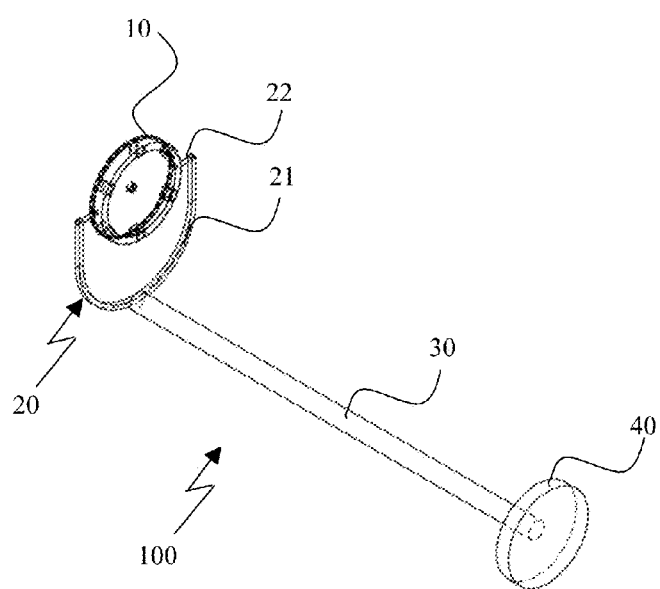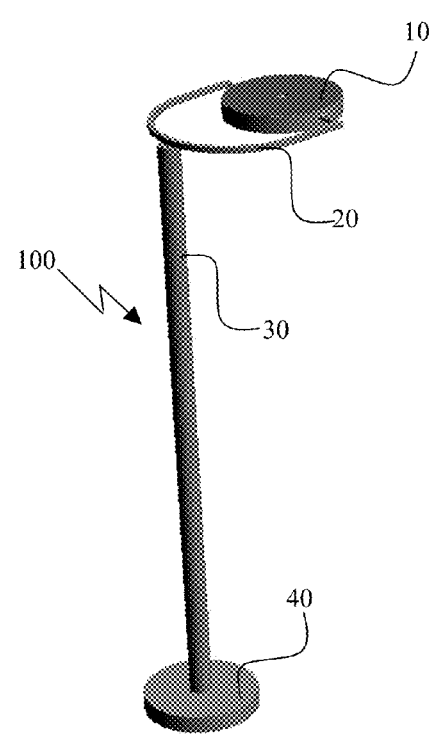
Fig. 4A
Fig. 4B

PHYSICAL MEANS AND METHODS FOR INDUCING REGENERATIVE EFFECTS ON LIVING TISSUES AND FLUIDS

FIELD OF THE INVENTION

The invention relates the field of non thermal plasma technology and application. The invention also relates to means and methods for inducing therapeutic or regenerative or beneficial effects on living tissues and fluid and gas media.

BACKGROUND OF THE INVENTION

Thermal plasmas and lasers have been widely used in medicine to cut tissues through heating. The effects of such thermal plasmas on tissues are non-selective and difficult to control because they occur primarily through transfer of intense heat. In contrast, non-thermal plasma does not produce heat, thus its effects are more selective. Although electrical discharges that generate non-thermal plasma have been known for a long time, their clinical potential has been largely ignored and until recently, applications have been confined to sterilization of inert surfaces or modulation of cell attachment. The exploitation of cold plasma for clinical applications requires the mechanistic understanding of the interaction of non-thermal plasma with living tissues.

US patent application 2010/0130911 describes a plasma source device which provides a reduced pressure in the ionization chamber. This device is adapted for the sterilization of wounds. Patent application WO2005/084569 discloses a disposable gas plasma tissue resurfacing instrument for skin treatment comprising an electromagnetically resonant focusing element. The aforementioned patent applications pertain to treating the tissues on the surface of wounds.

It has been shown that non-thermal plasma created by dielectric barrier discharge (DBD) has dose-dependent effects on mammalian cells in culture that range from increasing cell proliferation to inducing apoptosis. It has been further shown that these effects are primarily due to the formation of intracellular reactive oxygen species (ROS), which are known to cause DNA damage (S. Kalghatgi, C. Kelly, E. Cerchar, A. Fridman, G. Friedman, J. Azizkhan-Clifford, Effects of Non-Thermal Plasma on Mammalian Cells PLoS ONE, 21 Jan. 2011. 6(1)). US patent application 2010/0145253 relates to application of non thermal plasma to living tissue in vitro. Thus means and methods for inducing a regenerative effect on a whole subject, in vivo, using non thermal gas plasma treatment are still required.

The influence of plasma treatment on seed germination has recently been studied (I. Filatova et al. The effect of plasma treatment of seeds of some grain and legumes, on their sowing quality and productivity, *Rom. Journ. Phys. Vol.* 56, 139-143, 2011; S. Bozena et al, Influence of plasma treatment on wheat and oat germination, *IEEE Transactions on plasma science*, vol. 38, 2010). These studies describe an apparatus comprising a vacuum chamber, a rotary pump and a microwave resonator. The exposure time to the plasma treatment was for a period of several minutes to more than 40 min. Furthermore, the effects reported by these studies mainly relate to the seed coat surface and seed coat sterilization.

There is therefore a long felt and unmet need to provide systems and methods for inducing a regenerative effect on a subject, using efficacious non thermal gas plasma treatments and protocols which can be applied conveniently.

SUMMARY OF THE INVENTION

The present invention relates to the field of non thermal plasma technology and application. In particular, the invention relates to means and methods for inducing therapeutic or regenerative or beneficial effects on living tissues and fluid and gas media.

It is thus an object of the invention to disclose a system for the administration of plasma modified field (PMF) to a subject. The system comprises, inter alia, (a) a non thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. It is within the scope that the first surface of the plasma beam dish is mounted with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field, and any combination thereof. It is also within the scope that the PMFCM and the controller are configured to adjust any of the at least one coupling and reflecting element in a predetermined manner thereby providing the PMF for inducing a therapeutic or regenerative or beneficial effect on the subject.

It is another object of the invention to disclose the system for the administration of plasma modified field (PMF) as defined above, wherein the controller is further adapted to provide pulses of the PMF in a predetermined manner.

It is another object of the invention to disclose the system for the administration of plasma modified field (PMF) as defined above, wherein the NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

It is another object of the invention to disclose the system for the administration of plasma modified field (PMF) as defined above, wherein the at least one coupling element at least partially comprises Polyvinylidene fluoride, polyvinylidene difluoride (PVDF), PZT, lead zirconium titanate, ferroelectric oxides, Pb[Zr(x)Ti(1-x)]$O_3$, Pb$ZrO_3$, Barium Titanate (Ba$TiO_3$), (Ba, Sr)$TiO_3$, Ba(1-x) Sr(x)$TiO_3$, a ferroelectric material characterized by at least one of piezoelectricity, pyroelectricity and memory properties, a permanent magnet, an electromagnet, a superconducting magnet, Cobalt, Magnetite (Fe$_3$O$_4$), α-ferrite (a Fe), iron, ferromagnetic alloys, piezomagnetic ferrite materials, magnetoelectric ceramic materials and any combination thereof.

It is another object of the invention to disclose the system for the administration of a plasma modified field (PMF) as defined above, wherein the at least one reflecting element at least partially comprises a material or element selected from the group consisting of: high-reflector coating, metals such as iron and alloys thereof, stainless steel, aluminum, silver, gold and mixtures thereof, dielectric coating, extreme ultraviolet coating, high energy UV, glass, amorphous (non-crystalline) solid materials, polymers and any combination thereof.

It is another object of the invention to disclose the system for the administration of a plasma modified field (PMF) as defined above, wherein the at least one coupling element is arranged in at least one set of pairs or triplicates or in at least one set of more than three coupling elements.

It is another object of the invention to disclose the system for the administration of a plasma modified field (PMF) as defined above, wherein the at least one pair of coupling elements is positioned such that the poles of the coupling elements having attractive polarities or repulsive polarities.

It is another object of the invention to disclose the system for the administration of a plasma modified field (PMF) as defined above, wherein the PMF is applied in a manner selected from the group consisting of: a pulsed manner, a continuous manner, a series of pulses having predetermined rates and duration, a series of pulses characterized by a constant frequency value, a series of pulses characterized by increasing duration and increasing pulse intervals, a series of nanosecond or millisecond or second pulses and in any combination thereof.

It is another object of the invention to disclose the system for the administration of a plasma modified field (PMF) as defined above, wherein the applied PMF is characterized by at least one parameter selected from the group consisting of: a dose range of between about 0.1 J/cm$^2$ to about 4 J/cm$^2$, a frequency range of between about 100 Hz and about 20 MHz, a relative dielectric constant in the range of between about 500 and about 2500, a piezoelectric charge constant in the range of between about 100 ($10^{-12}$ C/N or $10^{-12}$ m/V) to about 1000 ($10^{-12}$ C/N or $10^{-12}$ m/V), a piezoelectric voltage constant in the range of between about 5 ($10^{-3}$ Vm/N or $10^{-3}$ m$^2$/C) to about 50 ($10^{-3}$ Vm/N or $10^{-3}$ m$^2$/C), frequency constants in the range of between about 1000 (Hz.m or m/s) to about 5000 (Hz.m or m/s) and any combination thereof.

It is another object of the invention to disclose the system for the administration of a plasma modified field (PMF) as defined above, wherein the subject is selected from the group consisting of: human, animal, plant, flatworms, planaria, fluids, soil, minerals, media, gas, gas and liquid mixtures, gas mixtures, cells, tissues, tissue culture, organs and a combination thereof.

It is another object of the invention to disclose the system for the administration of a plasma modified field (PMF) as defined above, wherein the applied PMF is adapted to affect biochemical parameters selected from the group consisting of: brain related parameters, protein fingerprint or profile, enzymatic activity, protein crystallization, medical therapeutic effects, improved plant parameters, improved water parameters, improved air pollution parameters, improved fluid or gas parameters, treatment of gaseous emissions, ozone treatment, increased functional recovery after a disruptive effect, improved immune system, skin related parameters, wound healing, recovery from bacterial infection, recovery from viral infection, tissue regeneration, pain relief, antioxidant activity, improved rheological properties and any combination thereof.

It is another object of the invention to disclose the system for the administration of a plasma modified field (PMF) as defined above, wherein the system is adapted to induce a therapeutic effect on a disease or condition selected from the group consisting of: rheological properties of blood, autoimmune diseases, degenerative diseases, neurological diseases, neurodegenerative diseases or disorders, inflammatory diseases, cancer-related diseases, cardiovascular diseases, skin-related diseases or conditions, pain relief, antiaging, functional recovery after having a disruptive effect, bowel-related diseases, enteric diseases, attention disorder (ADHD) syndromes and any combination thereof.

It is another object of the invention to disclose the system for the administration of a plasma modified field (PMF) as defined above, wherein the skin-related diseases or conditions are selected from the group consisting of: wound, burn injury, fresh trauma wound, skin infections, skin injuries such as scratches or scraps, skin inflammatory disease, psoriasis, dermatitis, lupus, necrosis, gangrene, eczema, atopic dermatitis, chronic wounds, skin cells regeneration, wrinkles, acne, UV radiation diseases, skin cancer, malignancy, cancerous tissue, melanoma, nodular melanoma, Acral lentiginous melanoma, Lentigo maligna, Superficial spreading melanoma, basal cell carcinoma, Bowen's disease, infections wounds, ulcers, burn injuries, fresh trauma wounds, wound at a haemostasis stage, wound at an inflammation stage, wound at a granulation or proliferation stage, wound at a contracture stage, wound at an epithelisation stage, wound at cancerous stage and any combination thereof.

It is another object of the invention to disclose the system for the administration of a plasma modified field (PMF) as defined above, wherein the degenerative diseases or neurological diseases or neurodegenerative diseases or disorders thereof are selected from the group consisting of: Parkinson, Alzheimer, Huntington, Alzheimer, Amyotrophic lateral sclerosis (ALS), Friedreich's ataxia, Lewy body disease, Spinal muscular atrophy, Creutzfeldt-Jakob disease, Primary progressive aphasia (PPA), Progressive supranuclear palsy (PSP) (or the Steele-Richardson-Olszewski syndrome), Multiple system atrophy, Multiple sclerosis, Niemann Pick disease, Atherosclerosis, Cancer, Essential tremor, Tay-Sachs Disease, Diabetes, Heart Disease, Keratoconus, Keratoglobus, Inflammatory Bowel Disease (IBD), Prostatitis, Osteoarthritis, Osteoporosis, Rheumatoid Arthritis, Chronic traumatic encephalopathy, Chronic Obstructive Pulmonary Disease (COPD) and Marfan's Syndrome.

It is another object of the invention to disclose the system for the administration of a plasma modified field (PMF) as defined above, wherein the protein fingerprint or profile is associated with a cellular pathway or a protein selected from the group consisting of signal transduction, stress response, cell cycle, antioxidation, DNA repair, replication, blood plasma proteins, glycoproteins, lypoproteins, Transferin, Serum Amyloid A, XPA, PKB, IMP, MMR, XPA, hTLRs, NE, Transthyretin, LRR, Ku, NLR, catalase, superoxide dismutase, peroxidases, PAT, LTP, Apm1, NLR, LPAF, beta glucanses, Ferredoxin and any combination thereof.

It is another object of the invention to disclose the system for the administration of a plasma modified field (PMF) as defined above, wherein the plant parameters are selected from the group consisting of plant vigor, plant growth, fruit size, fruit yield, improved root system, stress tolerance, stem height, seed germination and any combination thereof.

It is another object of the invention to disclose the system for the administration of a plasma modified field (PMF) as defined above, wherein the improved fluid or gas parameters are selected from the group consisting of: oxidation effect, induction of degradation of organic compounds, water or gas purification, destruction of pathogens such as bacteria and viruses, clearing radioactive isotopes and heavy metals, sterilization, pH values, hydrogen peroxide values, water or gas disinfection, water or gas contamination parameters, effect on mineral ions such as calcium and magnesium, oxidation of inorganic ions and any combination thereof.

It is another object of the invention to disclose the system for the administration of a plasma modified field (PMF) as defined above, wherein the system is adapted to provide an effect in vivo and in vitro.

It is another object of the invention to disclose a method for generating a plasma modified field (PMF), comprising steps of: (a) providing a system for the administration of a plasma modified field (PMF) to a subject as defined in any of the above; and (b) operating the system. The aforementioned method further comprises a step of configuring the PMFCM and the controller to adjust any of the at least one coupling and reflecting element in a predetermined manner thereby generating the PMF.

It is another object of the invention to disclose a method for inducing a therapeutic or regenerative or beneficial effect on a subject comprising the steps of: (a) providing a system for the administration of a plasma modified field (PMF) to a subject as defined in any of the above; and (b) applying the PMF to the subject in a predetermined manner. The aforementioned method further comprises a step of configuring the PMFCM and the controller to adjust any of the at least one coupling and reflecting element in a predetermined manner thereby providing the PMF for inducing a therapeutic or regenerative or beneficial effect on the subject.

It is another object of the invention to disclose a use of a system for the administration of a plasma modified field (PMF) to a subject. The use comprising steps of providing a system with: (a) a non thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core embodiment, the method comprises an additional step of mounting the first surface of the plasma beam dish with: (i) at least one coupling element; and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field, and (4) at least one piezomagnetic element for providing the field. The aforementioned use comprises an additional step of configuring the PMFCM and the controller to adjust any of the coupling and reflecting element in a predetermined manner thereby providing the PMF for inducing a therapeutic or regenerative or beneficial effect on the subject.

It is another object of the invention to disclose a method of manufacturing a system for the administration of a plasma modified field (PMF) to a subject comprising steps of assembling a system by steps of providing: (a) a non thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core aspect, the method comprises an additional step of mounting the first surface of the plasma beam dish with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing the field. The aforementioned use comprises an additional step of configuring the PMFCM and the controller to adjust any of the coupling and reflecting element in a predetermined manner thereby providing the PMF for inducing a therapeutic or regenerative or beneficial effect on the subject.

DETAILED DESCRIPTION OF THE FIGURES

In order to better understand the invention and its implementation in practice, a plurality of embodiments will now be described, by way of non-limiting example only, with reference to the accompanying drawings, wherein FIG. 1 is presenting in an out-of-scale-manner a schematic illustration of preferred embodiments of the system for the administration of a plasma modified field (PMF) to a subject;

Figure 5A:
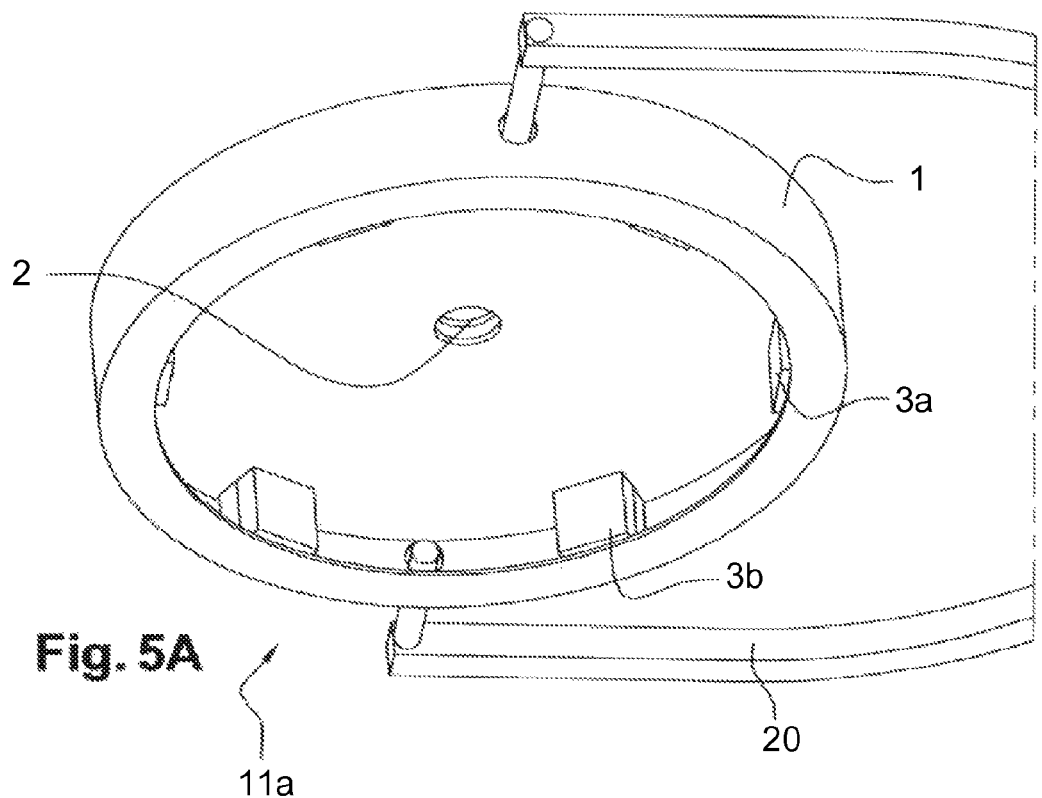
Figure 5B:
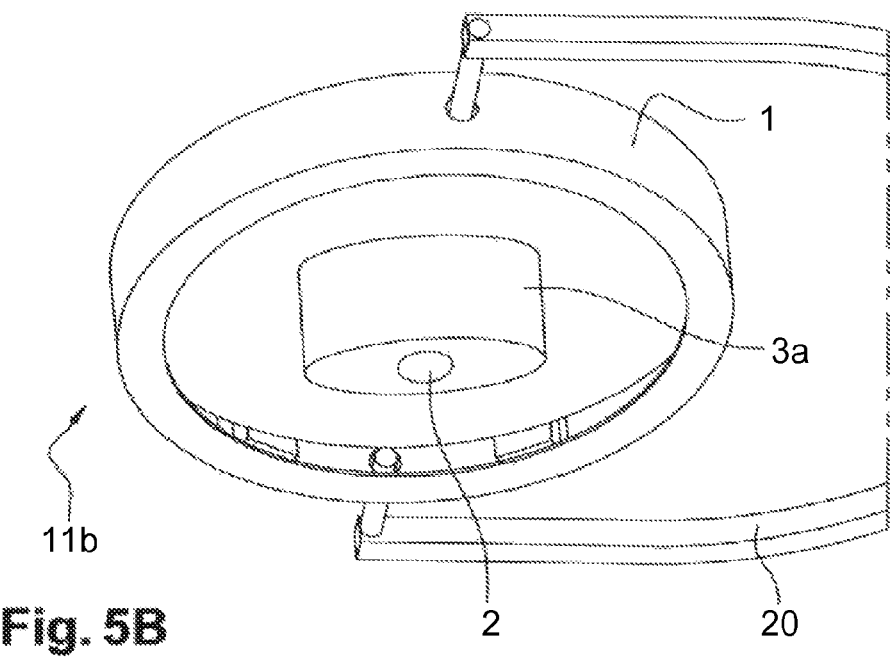
Figure 6:
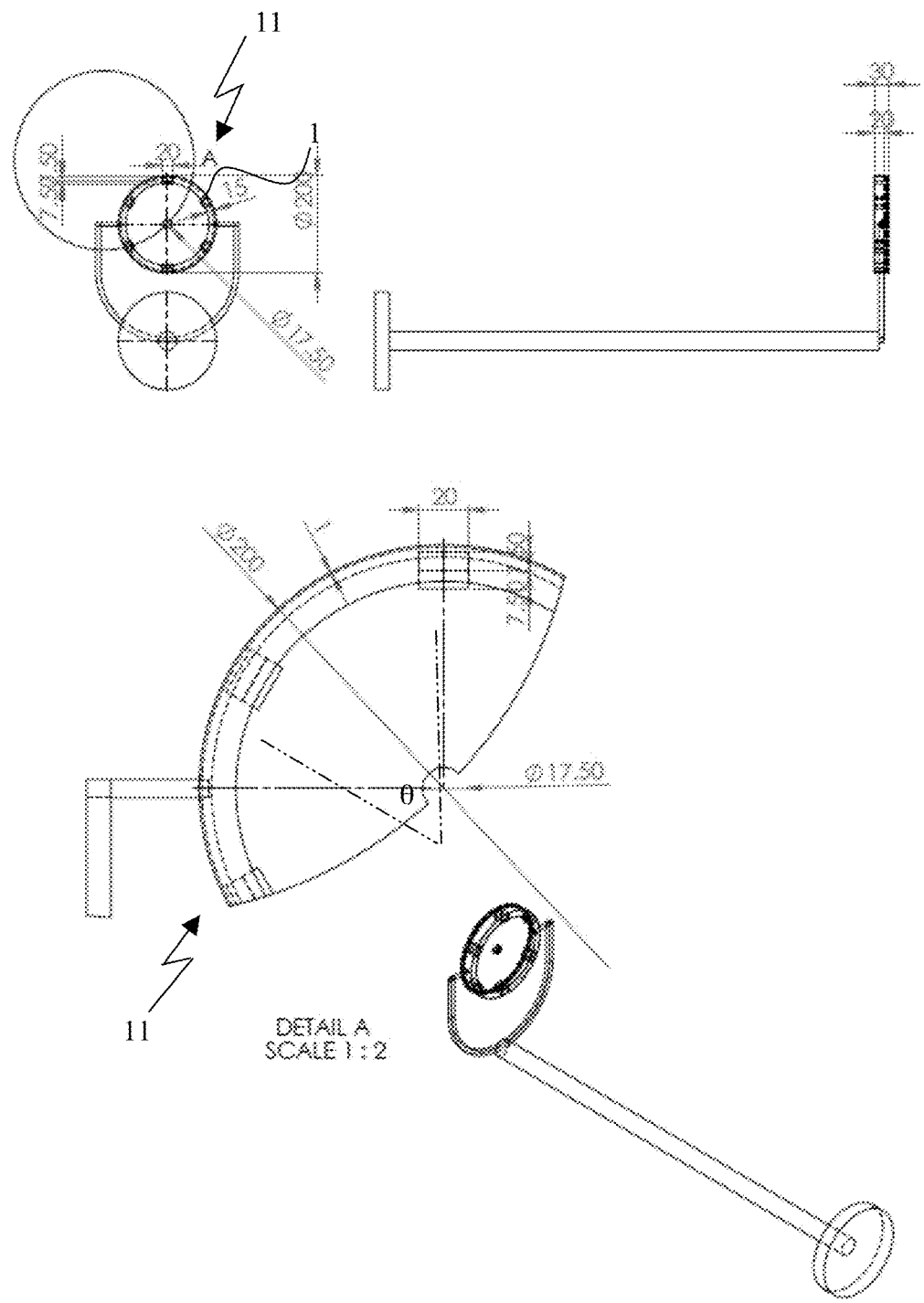
Figure 7A:
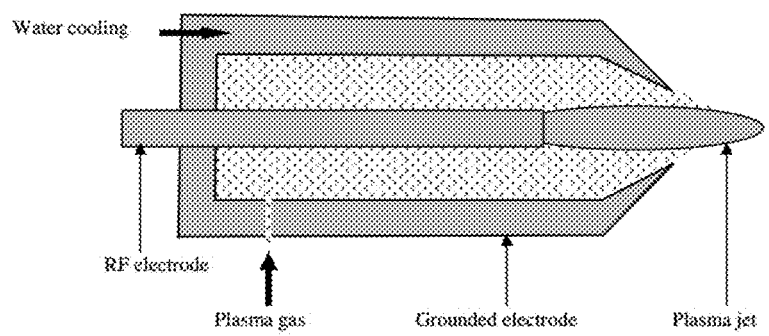
Figure 7B:
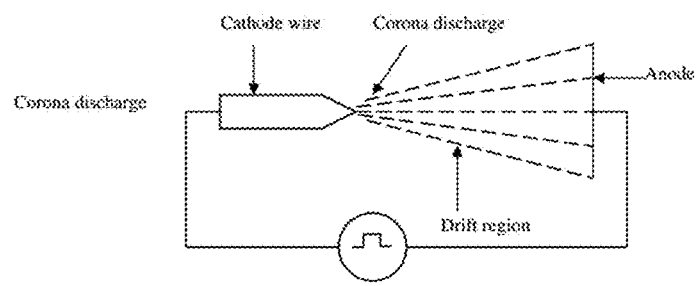
Figure 8:
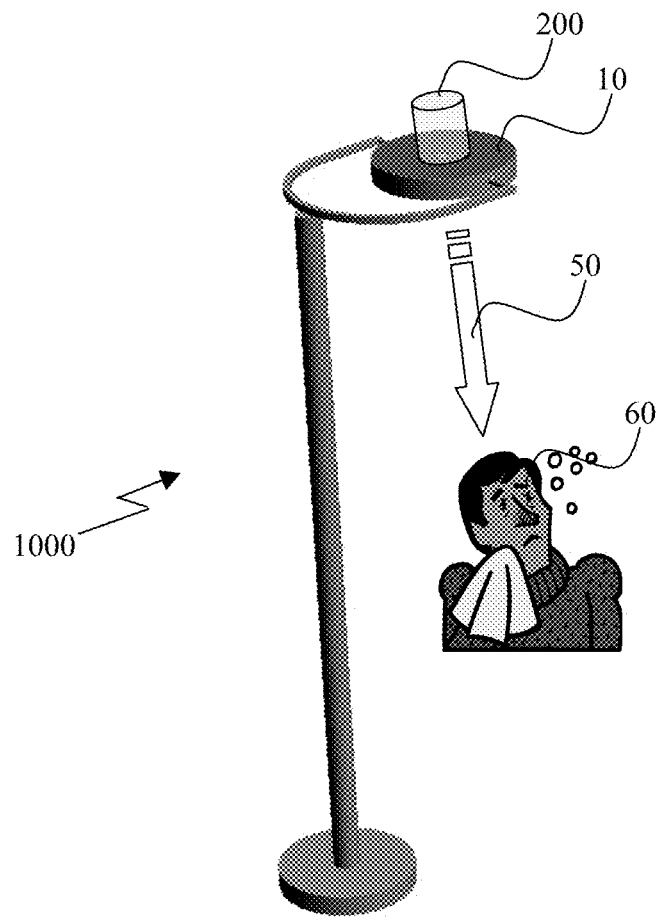

FIGS. 4A and 4B both illustrate in an out-of-scale-manner schematic views of a plasma beam dish (10) and stand thereof (100), FIG. 4A is a side view and FIG. 4BG is a perspective view;

FIGS. 5A and 5B are illustrating in an out-of-scale-manner schematic views of a multiple magnets plasma beam dish (11a) and a single magnet plasma dish (11b) as two embodiments of the present invention;

FIG. 6 is illustrating in an out-of-scale-manner schematic views of a plasma beam dish (11) according to a specific embodiment of the invention;

FIG. 7A is illustrating in an out-of-scale-manner a schematic view of an atmospheric pressure plasma jet as an alternative embodiment of the present invention; FIG. 7B is illustrating in an out-of-scale-manner a schematic view of a corona discharger as an alternative embodiment of the present invention;

FIG. 8 is illustrating in an out-of-scale-manner a schematic view of a system for applying a plasma modified field to a subject (1000) for inducing a therapeutic or regenerative or beneficial effect on the subject; and FIG. 9A-9F is illustrating in an out-of-scale-manner a schematic view of plasma modified field profiles, according to some embodiments of the invention, namely the profile of the intensity of the discharge over time.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide means and method for administering a plasma modified field (PMF) to a subject for inducing regenerative or therapeutic effects.

The present invention provides a system for the administration of a plasma modified field (PMF) to a subject. The aforementioned system comprising: (a) a non thermal plasma (NTP) emitting source for emitting a plasma beam; (b) a plasma modified field coupling mechanism (PMFCM) and (c) a controller for controlling said PMFCM. According to main aspects, the PMFCM comprises a plasma beam dish having at least one opening for the passage of said plasma beam; said plasma beam dish having a first surface and a second opposite surface; wherein the first surface of the plasma beam dish is mounted with: (i) at least one coupling element and (ii) at least one reflecting element. The at least one coupling element is preferably selected from the group consisting of: (1) at least one ferroelectric element for providing the field; (2) at least one ferromagnetic element for providing the field; (3) at least one piezoelectric element for providing the field; (4) at least one piezomagnetic element for providing the field and, any combination thereof. According to a core aspect of the invention, the PMFCM and the controller are configured to adjust any of the at least one coupling and reflecting element in a predetermined manner thereby providing the PMF for inducing a therapeutic or regenerative or beneficial effect on the subject.

It is further within the scope of the invention that the controller is configured to provide pulses of the PMF in a predetermined manner.

It is further within the scope of the invention wherein the unique system of the present invention, unexpectedly provides an effect beneath the outer integument of the treated subject. The relevant prior art relates to experiments showing surface modification (i.e. Feng et al., 2012. Appl. Phys. Lett. 101, 041602), particularly treating superficial wounds on the outer surface of the skin (epidermis) or affecting the seed coat or sterilization of the outer layer of the skin or seed. The present invention is further configured to induce a therapeutic or regenerative or beneficial effect on layers or tissues or regions not limited to the surface of the treated subject, for example affecting enteric diseases, providing an effect on cells or tissues in the brain or providing an effect on wounds penetrating to dipper layers of the skin and body.

It is further within the scope of the invention, wherein the system is adapted to provide a synergic effect with respect to inducing a therapeutic or regenerative or beneficial effect on the subject as compared to the effect induced by each of the plasma coupled elements, namely each of the at least one coupling element and at least one reflecting element, individually or in a partial combination administered.

In a further embodiment, the system is adapted to provide a synergic effect of at least about 5% in at least one of the properties of the PMF and/or with respect to inducing a therapeutic or regenerative or beneficial effect on the subject as compared to the properties of and/or the effect induced by each of the plasma coupled elements, namely each of the at least one coupling element and at least one reflecting element, individually or in a partial combination administered.

The term a "nonthermal plasma" or NTP generally refers hereinafter to any plasma which is not in thermodynamic equilibrium, either because the ion temperature is different from the electron temperature, or because the velocity distribution of one of the species does not follow a Maxwell-Boltzmann distribution. It is in the scope of the invention wherein the NTP is referred to by the specific technology used to generate it i.e. "gliding arc", "plasma pencil", "plasma needle", "plasma jet", "dielectric barrier discharge", "one atmosphere uniform glow discharge plasma", "atmospheric plasma", "ambient pressure nonthermal discharges", "nonequilibrium atmospheric pressure plasmas"; wherein those terms related to both: nonthermal plasma and plasma operated at or near atmospheric pressure.

It is further in the scope of the invention, wherein the generated plasma is selected from a group consisting of positive ions, negative ions, electrons metastables, atoms, free radicals and photons.

According to certain embodiments, the NTP emitting source is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

The term "dish" used herein generally refers to an article or element or object, preferably having a rounded-like or circular-like shape, such as a ring or a disk.

As used herein the term "about" denotes ±25% of the defined amount or measure or value.

The term "subject" as used herein refers to human, animal, plant, flatworms, planaria, fluids, soil, minerals, media, gas and liquid and gas mixtures and/or to an object.

The term "plasma modified field" or "PMF" as used herein refers to a plasma coupled to or modified or transformed by or generated by, at least one of ferroelectric means or elements, ferromagnetic means or elements, piezoelectric means or elements or by a combination of all elements or any partial combination thereof. According to a main embodiment, the plasma is further adjusted or influenced by a reflecting element as inter alio disclosed. It is within the scope of the present invention that a "plasma modified field" or "PMF" refers to plasma oscillations influenced by a coupling element selected from the group consisting of at least one ferroelectric element, at least one ferromagnetic element, at least one piezoelectric element or by any combination thereof, as well as by a reflecting element. The PMF is applied to a subject in a predetermined manner to induce a therapeutic or regenerative or beneficial effect.

In one embodiment, the PMF is applied to the subject in a predetermined mode, particularly pulse mode, which is determined or more specifically adjusted according to the classification (i.e. taxonomic classification) of the treated subject. For example, a pulse profile designed to induce a regenerative or beneficial effect in a plant may be different (i.e. by pulse duration or pulse intervals or both) from the PMF pulse profile designed to induce a therapeutic or regenerative or beneficial effect in human and/or from the PMF pulse profile designed to induce a beneficial effect on water or gas.

The term "coupling element" as used herein refers to means including a material or a substance or a component or a pattern that is used to provide the PMF. In preferred embodiments, the coupling element is selected from the group consisting of (1) at least one ferroelectric element; (2) at least one ferromagnetic element; (3) at least one piezoelectric element; (4) at least one piezomagnetic element and any combination thereof. According to certain embodiments, such coupling element or any combination of the aforementioned coupling elements are used as part of the system for the administration of a plasma modified field (PMF) to a subject to induce a therapeutic or regenerative or beneficial effect on said subject. The at least one coupling element is designed to provide an electric and/or magnetic field.

The term "ferromagnetic element" used herein refers to an element comprising a material which exhibit ferromagnetism in the broad sense that includes ferrimagnetism. According to certain aspects, the ferromagnetic element is selected from the group consisting of a permanent magnet, an electromagnet, a superconducting magnet, and any combination thereof.

It is within the scope of the invention that such materials include elemental metals, and in other embodiments include alloys, oxides or other chemical compounds or mixtures thereof. Non limiting examples of Ferromagnetic materials include Chromium(IV) oxide, Cobalt, Dysprosium, Ferrite (iron), Ferrite (magnet), Magnetite ($Fe_3O_4$), α-ferrite (a Fe), Gadolinium, Gallium manganese arsenide, Iron, Neodymium magnet, Nickel, Permalloy, Rare-earth magnet, Samarium-cobalt magnet, Suessite, Yttrium iron garnet, ferromagnetic alloys and any combination thereof.

The term "ferroelectric element" used herein generally refers to a material having a property of a spontaneous electric polarization that can be reversed by the application of an external electric field. In other words, ferroelectric materials refer to materials that maintain a permanent electric polarization that can be reversed, or switched, in an external electric field. In specific embodiments, ferroelectric materials are pyroelectric and inherently piezoelectric. In certain embodiments, ferroelectric capacitors may have the combined properties of memory, piezoelectricity, and pyroelectricity. According to some aspects, piezoelectricity generally refers to the generation of a surface charge in response to the application of an external stress to a material. According to further aspects, pyroelectricity generally refers to a change in the spontaneous polarization of a material in response to a change in temperature.

It is within the scope of the present invention that ferroelectric materials and/or elements include ferroelectric polymers, particularly polyvinylidene fluoride, or polyvinylidene difluoride (PVDF). In alternative embodiments, ferroelectric elements included within the scope of the present invention may at least partially comprise PZT, lead zirconium titanate, ferroelectric oxides, Pb[Zr(x)Ti(1-x)]O3, PbZrO3, Barium Titanate (BaTiO3), (Ba, Sr)TiO3, Ba(1-x) Sr(x)TiO3 and any combination thereof.

The term "piezoelectric element" used herein generally refers to materials or certain crystals having the ability to generate a voltage in response to applied mechanical stress. PZT (lead—zirconia-titanate) is one of a large family of materials, whose structure change on the application of an electric current or, when strained, generate electricity. These specific piezo or ferroelectric effects have the properties that when a current is applied, a volume change occurs in the material.

Thus it is herein acknowledged that according to one embodiment, an important ferroelectric material is lead zirconate titanate (PZT), which is part of the solid solution formed between ferroelectric lead titanate and anti-ferroelectric lead zirconate. Different compositions of PZT are used for different applications. For example, for memory applications, lead titanate is preferred, whereas piezoelectric applications make use of the diverging piezoelectric coefficients associated with the morphotropic phase boundary.

It is further within the scope of the present invention that piezoelectric transformers formed from the ferroelectric material Pb(ZrTi)O3 (PZT) are high voltage generators in which interactive electrical-mechanical energy conversion occurs based on piezoelectric effect.

It is herein further acknowledged that PZT (Lead zirconium titanate) is an inorganic compound with the chemical formula Pb[ZrxTi1-x]O3 0≤x≤1). It is a ceramic perovskite material that shows a marked piezoelectric effect, which finds practical applications in the area of electroceramics. It is a perovskite crystal structure, each unit of which consists of a small tetravalent metal ion in a lattice of large divalent metal ions. In the case of PZT, the small tetravalent metal ion is usually titanium or zirconium. PZT materials exhibit improved properties such as high sensitivity, high operating temperature, high dielectric constants and low dielectric loss, i.e. in comparison to the metallic oxide based piezoelectric material Barium Titanate (BaTiO3).

The term "piezomagnetic element" used herein generally refers to antiferromagnetic crystals and materials, such as Piezomagnetic ferrite materials, magnetoelectric ceramic materials (e.g., $Ba_{6/x}R_{2x}(Nb_{1/x}Fe_{2+x})O_3$), nickel, Ni—Fe alloy, V—Fe alloy, Fe—Co—Ni alloy, Ni—Cr—V alloy, (Fe, Cu system) Monel alloy; nickel ferrite, nickel-copper ferrite, nickel-zinc ferrite, composition systems including magnesium-manganese ferrite, nickel-cobalt ferrite etc. Piezomagnetizem may be characterized by a linear coupling between the system's magnetic polarization and mechanical strain. In a piezomagnetic, one may induce a spontaneous magnetic moment by applying physical stress, or a physical deformation by applying a magnetic field, see IEEE Std 319-1990 (1991), IEEE Standard on Magnetostrictive Materials: Piezomagnetic Nomenclature, which is incorporated herein as a reference. Moreover, it is further in the scope of the invention wherein at least one or more members of a group comprising magnetostrictive, electromagnetic, piezoelectric, and electrostrictive transducers and elements thereof are utilized.

The term "reflecting element" used herein generally refers to a component at least partially comprising a material selected from the group consisting in a non-limiting manner of: high-reflector coating, glass or amorphous (non-crystalline) solid materials, polymers, metals such as iron and alloys thereof, stainless steel, aluminum, silver, gold and mixtures thereof, dielectric coating, extreme ultraviolet coating, high energy UV and any combination thereof. Further examples of materials used as reflecting elements within the scope of the present invention may include: Titanium, Vanadium, Chromium, Yttrium, Zirconium, Niobium, Molybdenum, Technetium, Ruthenium, Rhodium, Palladium, Silver, Tantalum, Tungsten, Rhenium, Osmium, 0 Iridium, Platinum, Gold, Thallium, Lead, diamond-like carbon (DLC), graphite-containing materials, mixtures, blends and/or alloys thereof.

In other embodiments, a reflecting element refers to a device, surface or portion thereof that at least minimally reflects light or a plurality of wavelengths, back to its source with e.g., a minimum of scattering. In specific embodiments, an electromagnetic wave is reflected, in at least minimal extent, back along a vector that is parallel to but opposite in direction from the wave's source. Retroreflectors are devices that operate by returning light back to the light source along the same light direction. The coefficient of luminous intensity, RI, is the measure of a reflector performance, which is defined as the ratio of the strength of the reflected light (luminous intensity) to the amount of light that falls on the reflector (normal illuminance).

According to a certain aspect of the invention, aluminum serves as a good reflector (approximately 92%) of visible light and an excellent reflector (as much as 98%) of medium and far infrared radiation.

The term "reflecting element" may also refer to an optical coating, which generally means one or more thin layers of material deposited on at least a portion of an optical component such as a lens or mirror, which alters the way in which the optic reflects and transmits light. In a specific embodiment, high-reflector coating can be used to produce mirrors which reflect greater than 99.99% of the light which falls on them. More complex optical coatings exhibit high reflection over some range of wavelengths, and anti-reflection over another range, allowing the production of dichroic thin-film optical filters. The simplest optical coatings are thin layers of metals, such as aluminium, which are deposited on substrates to make mirror surfaces. The metal used determines the reflection characteristics of the mirror; aluminium for example, yields a reflectivity of around 88%-92% over the visible spectrum; silver, which has a reflectivity of 95%-99% even into the far infrared, exhibits a decreased reflectivity (<90%) in the blue and ultraviolet spectral regions; gold, which gives excellent (98%-99%) reflectivity throughout the infrared, has a limited reflectivity at wavelengths shorter than 550 nm.

According to certain embodiments, aluminium mirror coating has the highest reflectance of any metal in the 200-400 nm (UV) and the 3,000-10,000 nm (far IR) regions; in the 400-700 nm visible range it is slightly outperformed by tin and silver and in the 700-3000 (near IR) by silver, gold, and copper. Nevertheless, according to certain embodiments of the invention, the reflecting elements as defined in any of the above are low-reflection (LR) members and structural elements of the device, adapted to reflect UV, visible light and/or IR in a very minor measure (e.g., less than 7.5%).

In alternative embodiments, high-reflection (HR) coatings are usually based on the periodic layer system composed from two materials, one with a high index, such as zinc sulfide (n=2.32) or titanium dioxide (n=2.4) and low index material, such as magnesium fluoride (n=1.38) or silicon dioxide (n=1.49). This periodic system significantly enhances the reflectivity of the surface in the certain wavelength range called band-stop, whose width is determined by the ratio of the two used indices, while the maximum reflectivity is increasing nearly up to 100% with a number of layers in the stack. The thicknesses of the layers are generally quarter-wave designed such that reflected beams constructively interfere with one another to maximise reflection and minimize transmission. Coatings built-up from deposited dielectric lossless materials can reach reflectivities greater than 99.999%, over a relatively narrow range of wavelengths. Common HR coatings can achieve 99.9% reflectivity over a broad wavelength range (tens of nanometres in the visible spectrum range).

Multilayer mirrors that are constructed of hundreds of alternating layers of a high-mass metal such as molybdenum or tungsten, and a low-mass spacer such as silicon, vacuum deposited onto a substrate such as glass, causes the mirror to reflect EUV light (wavelengths shorter than about 30 nm) of the desired wavelength as would a normal metal mirror in visible light. Using multilayer optics it is possible to reflect up to 70% of incident EUV light (at a particular wavelength chosen when the mirror is constructed).

It is also within the scope of the invention that the system comprising the claimed elements of at least one coupling element and at least one reflecting element may operate and designed as a holographic prism, influencing the treated subject. In this embodiment the system comprising the reflecting element may simultaneously satisfy the requirements of high discreteness and accuracy. It is herein acknowledged that holographic prism-like elements or holograms has the advantage of high temperature stability, high efficiency, relatively small size and weight, and the ability to tolerate sharp changes in the optical and geometric characteristics (i.e. devitrification). In other aspects, the system for the administration of PMF is designed and operated as a diffraction grating device.

According to certain aspects, the at least one reflecting-element component of the system of the present invention is configured to focus and enhance the plasma modified field. According to other aspects, the at least one reflecting element is configured to centralized and/or gather and/or reduce loss of the generated plasma modified field. According to a still other aspect of the invention, the at least one reflecting element is configured to increase the efficiency of the discharged plasma modified field. Furthermore, without wishing to be bound by theory, the system comprising the at least one reflecting element is designed to adjust and to balance the energetic resonance of the PMF interacting with the treated object or subject.

Reference is now made to magnetohydrodynamics (MHD) (magneto fluid dynamics or hydromagnetics) as an aspect of the present invention. This embodiment refers to the studies of the dynamics of electrically conducting fluids. Examples of such fluids include plasmas, liquid metals, and salt water or electrolytes. It is herein acknowledged that the fundamental concept behind MHD is that magnetic fields can induce currents in a moving conductive fluid, which in turn creates forces on the fluid and also changes of the magnetic field itself. The set of equations which describe MHD are a combination of the Navier-Stokes equations of fluid dynamics and Maxwell's equations of electromagnetism. Magnetohydrodynamics (MHD) is the physical-mathematical framework that concerns the dynamics of magnetic fields in electrically conducting fluids, e.g. in plasmas and liquid metals.

The term "brain" as used herein refers to brain cell types including neurons (also known as nerve cells) and glial cells; brain lobes including the frontal lobe, parietal lobe, occipital lobe, and temporal lobe; and brain tissues including the cortex, cranium, basal ganglia, brain stem, cerebellum, dura, the spinal cord and brain membranes and outer parts of the brain, including the meninges.

The term "unit discharge" as used herein refers to the voltage oscillation at a time.

It is according to one embodiment of the invention wherein a system for the administration of a plasma modified field (PMF) to a subject is provided. This system comprises, inter alio, modules as follows: a non-thermal gas plasma emitting source for emitting a plasma beam and a plasma modified field coupling mechanism (PMFCM). The PMFCM comprises, inter alio, a plasma beam dish having at least one opening for the passage of said plasma beam; said plasma beam dish having a first surface and a second opposite surface; said first surface of said plasma beam dish is mounted with: (i) at least one coupling element preferably selected from the group consisting of: (1) at least one ferroelectric element for providing the field; (2) at least one ferromagnetic element for providing the field; (3) at least one piezoelectric element for providing the field; and (4) at least one piezomagnetic element for providing the field and, (5) a combination thereof; and (ii) at least one reflecting element. The system further comprises at least one controller for controlling said PMFCM. In this way, the PMFCM and the controller are configured to adjust any of the at least one coupling and reflecting element in a predetermined manner thereby providing the PMF for inducing a therapeutic or regenerative or beneficial effect on the subject.

It is according to a main embodiment of the invention wherein the PMFCM is adapted to couple the plasma beam with at least one of a ferroelectric element, a ferromagnetic element, a piezoelectric element or any combination thereof. Thus the present invention uniquely provides a mechanism for discharging plasma modified field (PMF), in a predetermined manner for inducing therapeutic and/or regenerative and or beneficial effects on a subject.

It is according to another embodiment of the invention wherein the system is designed and operated to a remote or indirect treatment of the object; Gadri et al., 2000. Surface Coatings Technol 131:528-542 and Laroussi and Lu, 2005. Appl. Phys. Lett. 87:113902 and Montie et al., 2000. IEEE Trans Plasma Sci 28:41-50 and Topala and Nastuta, 2012. Plasma for Bio-Decontamination, Medicine and Food Security, NATO Science for Peace and Security Series A: Chemistry and Biology. ISBN 978-94-007-2851-6. Springer Science+Business Media B.V., p. 335 and Middelkoop et al. Burn wound healing: a role for plasma medicine? and Vasile Nastuta et al., 2011. Journal of Physics D: Applied Physics. 44(10):105204; are publications incorporated herein as a reference and non limiting examples of NTP. This type of NTP in use is, e.g. a decaying plasma (afterglow)-longer lived chemical species. The NTP density and energy is e.g., of a moderate density—subject is located remote from electrodes. However, a larger volume of NTP can be generated using multiple electrodes. The spacing of target from NTP-generating electrode is approx. 5 to 20 cm; particularly 15 cm arcing (filamentous discharge) unlikely to contact subject at any power setting. In this system, there is no electrical conduction through target. The suitability for irregular surfaces is high—remote nature of NTP generation means maximum flexibility of application of NTP afterglow stream.

In other embodiments, the NTP in use is atmospheric pressure plasma jet (APPJ). The plasma may be generated using principles of corona discharge, DBD and microdischarges. Examples of applications of the NTP plasma or modified-plasma may include treatment of living cells or tissues, wound healing, cancerous cell apoptosis, blood coagulation i.e. on wounds, bone tissue modification, sterilization and decontamination. In such a case, the low temperature plasma jet is driven by high voltage pulses. In a specific embodiment, plasma jet works in helium. According to a main object, the system for administering modified plasma to a subject is applied to provide positive medical results related to recovery process of wounds i.e. of burned wounds, skin regeneration and re-epitelization.

It is according to another embodiment of the invention wherein the system is designed and operated to a direct treatment of the object; Lee et al., 2005. *Surface Coatings Technol* 193:35-38; Sladek and Stoffels, 2005. *J Phys D: Appl Phys* 38:1716-1721 and Stoffels et al., 2002. *Plasma Sources Sci. Technol.* 11:383-388 are publications incorporated herein as a reference and non limiting examples of systems designed and operated to a direct treatment. This type of NTP in use is, e.g., Active plasma—short and long-lived species. The NTP density and energy is e.g., Higher density—target in the direct path of a flow of active NTP. The spacing of target from NTP-generating electrode is approx. 1-5 cm; arcing can occur at higher power settings, can contact target. In this system, an electrical conduction through target is provided under a normal operation, but possible during arcing. The suitability for irregular surfaces is moderately high—NTP is conveyed to target in a directional manner, requiring either rotation of target or multiple NTP emitters.

It is according to another embodiment of the invention wherein the system is designed and operated in a method of electrode contact; Kelly-Wintenberg et al., 1999. *J. Vac. Sci. Technol.* A 17(4):1539-44; Laroussi et al., 2003. *New J Phys* 5:41.1-41.10; and Montenegro et al., 2002. *J Food Sci* 67:646-648 are publications incorporated herein as a reference and are provided as non limiting examples of embodiments included within the scope of the present invention. This type of NTP in use is, e.g., Active plasma—all chemical species, including shortest lived and ion bombardment. The NTP density and energy is e.g., highest density—target within NTP generation field. The spacing of target from NTP-generating electrode is approx. ≤1 cm; arcing can occur between electrodes and target at higher power settings. In this system, regarding the electrical conduction—the system is operatable e.g., if target is used as an electrode or if target between mounted electrodes is electrically conductive. The suitability for irregular surfaces is moderately low—close spacing is required to maintain NTP uniformity. However, electrodes can be shaped to fit a defined, consistent surface.

It is according to another embodiment of the invention wherein the system is designed and operated to discharge plasma generated by piezoelectric transformers (PTs). P. Rajasekaran et al., *Institute for electrical Engineering and Plasma Technology; Ruhr-Universitaet Bochum, Germany*; and Itoh et al. 2006. *Plasma Sources Sci. Technol.* 15 S51-S61, are publications incorporated herein as a reference and are provided as non limiting examples of embodiments included within the scope of the present invention. Such PT-based plasma reactors are herein shown to have various therapeutic and beneficial and regenerative effects. Example of piezoelectric transformers (PTs) used in the system of the present invention is of the material $Pb(ZrTi)O3$. PTs of $Pb(ZrTi)O3$ generate high voltage by the piezoelectric effect, which can cause excitation and ionization of atoms and molecules resulting in the generation of discharge plasma. In a specific embodiment, DBD occurs at atmospheric pressure and above between the PT surface and a dielectric metal having a metal back electrode. In this case an electro-mechanical energy conversion by the piezoelectric effect is related to the mechanical vibration of the PT and the resultant surface potential.

It is herein acknowledged that the piezoelectric transformers (PT)-based plasma reactors of the present invention are capable of generating various kinds of discharge plasma, including corona discharge, glow discharge and DBD at low voltages over a wide range of gas pressure.

It is according to another embodiment of the invention wherein the system is designed and operated to discharge non-thermal plasma created by high voltage pulsed power supply.

It is according to another embodiment of the invention wherein the system is designed and operated to discharge non-thermal plasma coupled to a magnetic field. Liu Jingjing et al. 2005. *Plasma Science & Technology* Vol. 7 No. 5 3073-3077; and Zongbao Feng et al., 2012 *App. Phys. Lett* 101 041602 are publications incorporated herein as a reference and are provided as non limiting examples of embodiments included within the scope of the present invention.

It is according to another embodiment of the invention wherein the system is designed and operated to discharge ferroelectric coupled non-thermal plasma field. Dunaevsky A. et al., 2001. *Journal of applied Physics* 90: 8 4108-4114; and Holzer F. et al., 2005. Plasma Chemistry and Plasma Processing 25:6 595-611, are publications incorporated herein as a reference and are provided as non limiting examples of embodiments included within the scope of the present invention.

It is according to another embodiment of the invention wherein the system is designed and operated to discharge non-thermal plasma coupled to at least one of the following: a magnetic field, an electric field or a combination thereof. Such a coupling mechanism (i.e. PMFCM) is herein demonstrated to have significantly increased or in other embodiments, synergistic effect with respect to efficiency and improved properties and results relative to applying non-thermal plasma deprived of the coupling mechanism (i.e. PMFCM).

Figure 1:
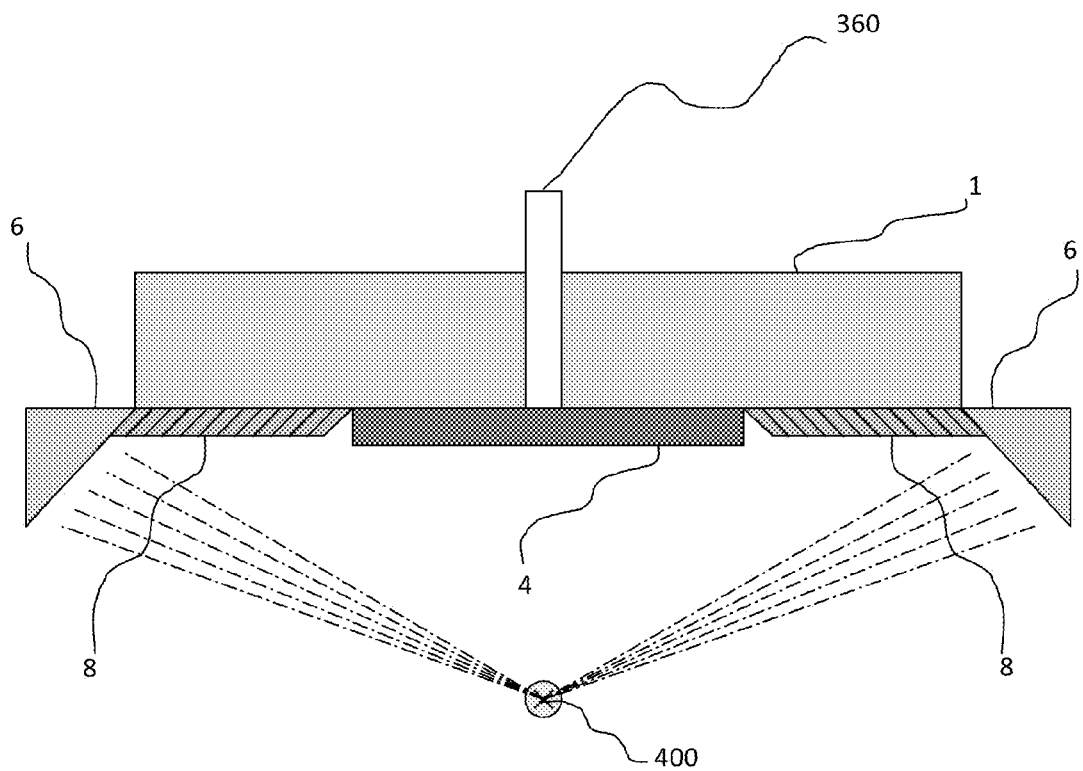

Reference is now made to FIG. 1 presenting a schematic illustration of an out-of-scale-manner of a cross section of preferred embodiments of the system for the administration of a plasma modified-field (PMF) to a subject. The figure presents elements mounted with the plasma beam dish. According to certain embodiments of the apparatus of the present invention, H.V. (high voltage) electrode (360), shown in FIG. 1, is energized by a high frequency, high voltage power source. The electrode (360) is protruding through the second surface of the plasma beam dish, preferably at least partially comprising a polymeric material. Non limiting examples of such polymeric materials may include polycarbonates, Polystyrene (PS), polyesters, polyphenylene oxide, acrylonitrile butadiene styrene (ABS), styrene acrylonitrile, polyimide and blends and polymeric combinations thereof. In this embodiment, the H.V. electrode 360 is positioned in the center of the plasma beam dish.

According to a specific embodiment, no voltage is applied to the treated object or subject (400). In this embodiment, the object (400) which may be a human or animal body or a plant or a liquid or gas sample, acts as a floating electrode, and the non-thermal plasma discharge may be referred to as a floating electrode dielectric barrier discharge (FE-DBD).

In an alternative embodiment, the plasma discharger is referred to as a H.V. negative DC corona.

Still in the embodiment presented in FIG. 1, the first surface of the plasma beam dish is mounted with a coupling mechanism (PMFCM) comprising elements configured to influence the H.V. NTP discharge. According to one embodiment, at least one coupling element (4), particularly a single coupling element (4) is disposed in the first surface of the plasma beam dish, i.e. in the center of the plasma beam dish. The at least one coupling element (4) together with the reflecting element (not shown) is configured to alter or modify or affect the plasma discharge, i.e. by improving the efficiency of the resulted modification over larger areas or to have more intense or marked effects, not limited to surface modification of the treated subject, but to affecting layers, areas or tissues beneath the outer integument of the treated subject The at least one coupling element (4) may be selected from the group consisting of: at least one ferroelectric element; at least one ferromagnetic element; at least one piezoelectric element; and any combination thereof. The plasma modified-field (PMF) (8) is discharged in a predetermined manner. The plasma beam dish is further mounted with at least one reflecting element (6). In this figure, the reflecting elements (6) are disposed in the outer rim of the plasma dish, i.e. in an opposite configuration. It is submitted that the reflecting elements have a significant and highly important effect on focusing and/or improving the modification area or efficiency applied by the plasma modified-field (PMF) (8) on subject 400. It is further submitted that the system as described herein comprising the at least one reflecting element is designed to adjust or adapt or balance the energetic resonance of the PMF interacting with, or discharged-received by the subject.

It is within the scope of the invention that the system of FIG. 1 can be adapted for ozone treatment i.e. decomposition.

Figure 2:
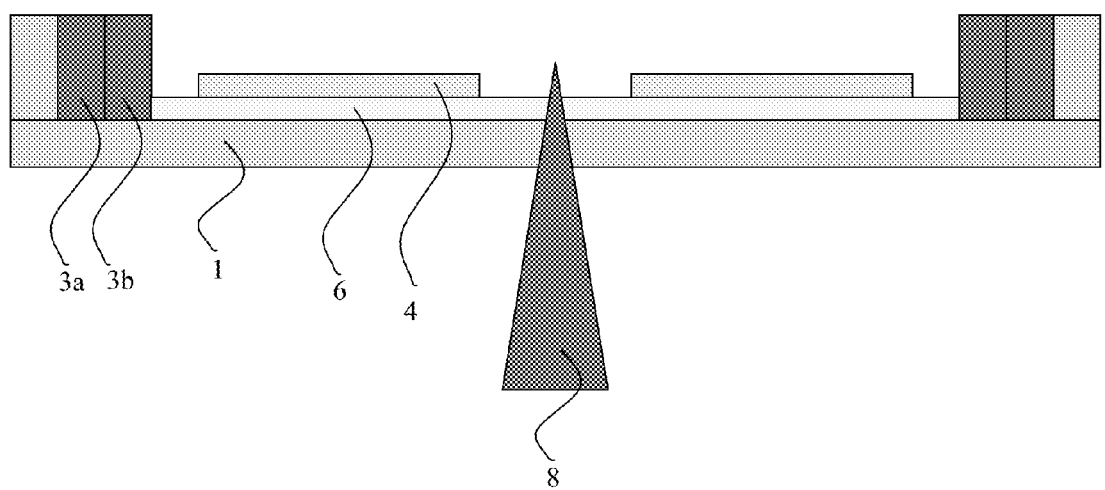
FIG. 2 is presenting in an out-of-scale-manner a schematic illustration of a cross section view of embodiments of the system for the administration of a plasma modified field (PMF) to a subject.

Reference is now made to FIG. 2 presenting in an out-of-scale-manner a schematic illustration of a cross section view of alternative embodiments of the system for the administration of plasma modified-field (PMF) to a subject. In this embodiment, a plasma beam dish having an opening for the passage of a NTP beam (8) is presented. The plasma beam dish has a first surface mounted with elements as disclosed hereinafter, and a second surface (1). The second surface (1) at least partially comprises a polymeric material. The first surface is mounted with at least one reflecting element (6). In this embodiment, the at least one reflecting element (6) is designed to be disposed as a ring like shape surrounding the plasma beam opening (8). At least one coupling element (4) is further disposed on said first surface of the plasma bean dish, preferably attached to the at least one reflecting element (6). As shown in FIG. 2, coupling elements (4) are disposed in pairs, in opposite orientation i.e. around the plasma beam opening (8). The coupling elements (4) may include ferroelectric and/or piezoelectric materials or elements or transformers. It is further presented in this figure that, ferromagnetic elements (3a and 3b) are disposed in the outer rim, or the distal part (relative to the plasma beam opening), of the plasma dish, preferably in the first surface of the plasma dish. In this embodiment, the ferromagnetic elements (3a and 3b) are disposed in pairs or sets containing two, three or more elements.

Figure 3:
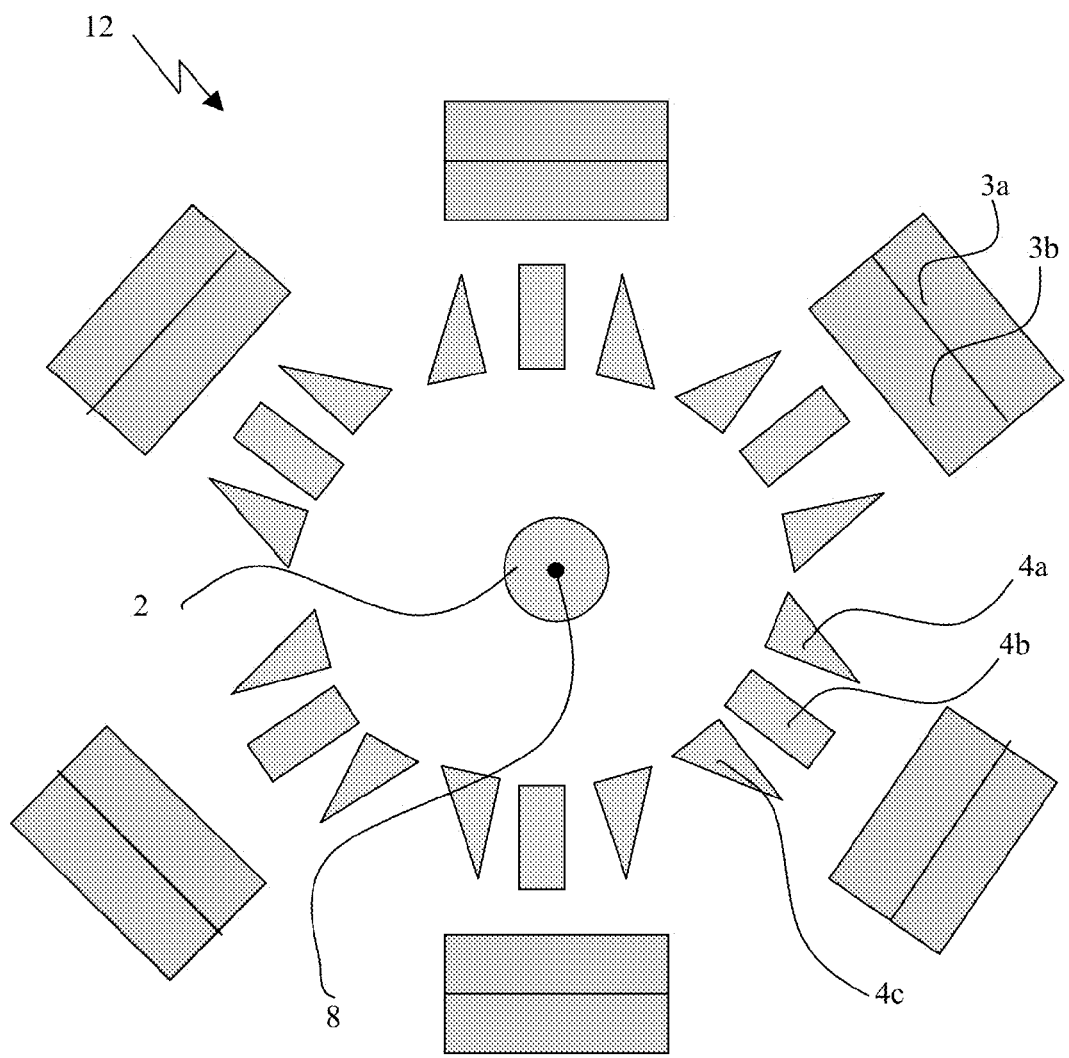
FIG. 3 is presenting in an out-of-scale-manner a schematic illustration of a top view of embodiments of the system for the administration of a plasma modified field (PMF) to a subject.

Reference is now made to FIG. 3 presenting in an out-of-scale-manner a schematic illustration of a top view of embodiments of the system as illustrated in FIG. 2. This figure presents elements mounted within the first surface of the plasma beam dish (12) comprising the PMFCM. According to one embodiment, the plasma dish (12) comprises a rounded structure. In more specific embodiments the plasma dish (12) having a diameter of about 15-20 cm. As can be seen, the elements are arranged radially around a central aperture (2) adapted for the passage of the plasma beam (8), particularly a high voltage negative DC corona discharger (not shown). The elements disclosed inter alia in combination with the at least one reflecting element (not shown) are designed to couple or modify or transform the plasma beam with at least one of a ferroelectric, a piezoelectric, ferromagnetic element or any combination thereof. The coupling elements comprising: ferroelectric and/or piezoelectric elements (4) disposed around the central aperture (2). According to certain embodiments, the coupling or transforming elements (4a, 4b, 4c) are arranged in sets of three elements per set, preferably disposed around the central aperture (2). As shown in this figure, each set of transforming elements (4a, 4b, 4c) is positioned opposite to at least one ferromagnetic element (3a, 3b). The ferroelectric elements are configured to couple the plasma beam (8) with a ferroelectric field.

In other embodiments shown in FIG. 3, ferromagnetic elements (3a, 3b) are arranged in pairs along the inner perimeter of the dish (12). In specific embodiments, six pairs of ferromagnetic elements are radially positioned in the outer rim of the first surface of the dish (12). In a further aspect of the invention, the at least one pair of ferromagnetic elements is made of ferromagnetic material, particularly, cobalt or cobalt alloy, iron and iron oxides as Fe3O4 such as samarium-cobalt magnet (e.g., $SmCo_5$, or SmCo Series 1:5; $Sm_2Co_{17}$, or SmCo Series 2:17), neodymium magnets, ferromagnetic, ferroelectric and ferrimagnetic materials, such as $Fe_3O_4$ magnetic ferrite, Alfa ferrite ($\alpha$-Fe) and beta iron ($\beta$-iron) or other paramagnetic substances or any combination thereof.

Thus the system is designed to generate a unique plasma modified-source driven by the synergic effect resulting from the combination of NTP (8) with at least one ferroelectric and/or piezoelectric element (i.e. (4a, 4b, 4c) and/or at least one magnetic field element (i.e. 3a, 3b), whereby these fields are combined with at least one reflecting element (shown in FIGS. 1 and 2).

According to one embodiment, the at least one coupling element (4) or ferromagnetic element (3a and 3b) is arranged radially around said plasma beam opening (8).

According to a further embodiment the at least one coupling element (4) or ferromagnetic element (3a and 3b) is arranged in sets of pairs or triplicates, around the plasma beam opening (8).

According to a further embodiment, the PMFCM comprises at least one pair of coupling elements (4) or ferromagnetic element (3a and 3b).

According to a further embodiment, the PMFCM comprises at least one pair of oppositely oriented coupling elements (4) or ferromagnetic element (3a and 3b).

According to a further embodiment, the PMFCM comprises at least one pair of oppositely oriented pairs of coupling elements (4) or ferromagnetic elements (3a and 3b).

According to a further embodiment, the at least one pair of coupling elements (4) or ferromagnetic elements (3a and 3b) is arranged in parallel orientation.

According to a further embodiment, the at least one pair of coupling elements (4) or ferromagnetic elements (3a and 3b) is positioned such that the poles of the coupling elements (4)

or ferromagnetic elements (3a and 3b) having attractive polarities or repulsive polarities.

It is well within the scope of invention wherein both (i) a plasma beam dish with a coupling element and (ii) a plasma beam dish deprived of a coupling element are disclosed. In those two embodiments, one or more coupling elements are mounted in an approximate centralized position on the first surface of the plasma dish. According to yet another embodiment, one or more coupling elements are designed as a disk having a diameter of approximately 0.5 to about 2.25 cm. In other embodiments one or more coupling elements made of or otherwise comprises material APC 841 or any suitable alternative, e.g., as defined in Table 1 below. A plasma field, emitted from an NTP source to the PMFCM comprising a plasma beam dish, is modified by at least one coupling element and discharged from the surface surrounding the coupling element. According to still another embodiment of the invention, a similar plasma beam dish, characterized by being deprived of a coupling element. Here, NTP beam discharges from the plasma dish via a centralized beam, whereas the plasma discharges from a reactor containing the coupling element affects a wider surface and a characterized by a higher intensity.

Thus the system for the administration of a plasma modified-field has many advantages. It is designed to generate and provide a highly efficient and highly powered plasma field, driven in parallel by at least one coupling element selected from a group consisting of: at least one piezoelectric element, at least one ferroelectric element, at least one magnetic element and any combination thereof, and by at least one reflecting element.

Reference is now made to FIGS. 4A and 4B, illustrating in an out-of-scale-manner a schematic view of a plasma beam dish (10) and stand thereof (100). Stand (100) reversibly- and maneuverable-immobilizing dish (10) in a predefined spatial location and 3D orientation, e.g., by means of one or more sets of arms (20) operatable mechanically (See arms 21 and 22) or otherwise electrically of hydraulically. Stand (100) further comprises, e.g. reciprocally or rotatably elongatable shaft (30), affixably mounted on a suitable base (40). Stand (100) is made of a suitable material, such as polymeric composition, metal ware, composite materials and any mixture and combination thereof.

Reference is now made to FIG. 5A and FIG. 5B which illustrate in an out-of-scale-manner a set of two schematic views of plasma beam dish (11a and 11b, respectively). Dish 11a comprises a plurality of magnets, here located at the circumference of the dish, whereas dish 11b comprises at least one (here-one) magnet, located, e.g., at the central inner portion of the said dish. Dish 11a comprises a rounded structure (1) with at least one central aperture (2), adapted by means of size and shape to accommodate within at least one plasma emitting source. Along the inner perimeter of the dish a plurality of coupling elements are affixed for coupling said plasma beam with an electromagnetic and/or ferroelectric and/or piezoelectric element. The plasma beam dish further comprises at least one reflecting element (not shown). According to a further aspect, the plasma beam is herein used to focus the at least one field generated by the at least one coupling element to provide a plasma modified field (PMF): see for example coupling elements 3a and 3b. The dish, as defined above, is 3D oriented and spatially arranged by means of immobilizing arms mechanism (20).

It is in the scope of the invention wherein the dish, particularly the second surface of the dish is made or comprises polymers, such as 70% Acrylonitride Butadiene Styrene (ABS) and Polysterene (PS). It is further in the scope of the invention wherein the dish is made of, or otherwise comprises, a mixture of polymers, such as 70% PS and 30% ABS (wt/wt or mole/mole).

Reference is now made to FIG. 6 illustrating in an out-of-scale-manner a various schematic views of a plasma beam dish (11) according to one embodiment of the invention. It is well within the scope of the invention wherein the external diameter of the dish is about 200 mm, the width of the perimeter rim (1) is 15 mm and dish width is 30 mm. These are non limiting examples of the plasma beam dish. In this embodiment, six coupling elements, i.e. magnets and/or ferroelectric elements are evenly applied along the dish perimeter (i.e., θ between element 3a and 3b is 60°). Nevertheless, it is well within the scope of the invention wherein one coupling element is applied, 2 to 4 coupling elements are applied, 4 to 12 coupling elements are applied and wherein 20 or less to 240 and more coupling elements are applied. Thus, the θ between coupling element 3a and 3b is varied between 0.5° to 270°.

It is in the scope of the invention wherein the coupling elements are set in pairs, each of which is arranged as a first coupling element and a second coupling element. Said first coupling element is located opposite to said second coupling element (θ between $1^{st}$ and $2^{nd}$ coupling elements is 180°).

It is further in the scope of the invention wherein at least one of the coupling elements, i.e. magnet is made of cobalt or cobalt alloy, such as samarium-cobalt magnet (e.g., $SmCo_5$, or SmCo Series 1:5; $Sm_2Co_{17}$, or SmCo Series 2:17), neodymium magnets, ferromagnetic, ferroelectric and ferrimagnetic materials, such as $Fe_3O_4$ magnetic ferrite, Alfa ferrite (α-Fe) and beta iron (β-iron); paramagnetic substances, such as platinum, aluminum, and oxygen; Diamagnetic means repelled by both poles. Compared to paramagnetic and ferromagnetic substances, diamagnetic substances, such as carbon, copper, water, and plastic and any mixtures and combinations thereof.

It is further in the scope of the invention wherein the dish comprises six coupling elements: positioned at 12 o'clock, 2 o'clock, 4 o'clock, 6 o'clock, 8 o'clock, and 10 o'clock. It is further in the scope of the invention wherein said 12 and/or 10 o'clock is a cobalt-containing coupling element, i.e. magnet. It is further in the scope of the invention wherein said 2 and/or 4 o'clock is a magnetite-type coupling element, i.e. magnet. It is further in the scope of the invention wherein said 6 and/or 8 o'clock is an alfa-ferrite-type coupling element, i.e., magnet.

It is further in the scope of the invention wherein the pairs of magnets' or the coupling elements poles are of S—S, N—N or S—N orientation.

It is further in the scope of the invention wherein the NTP plasma discharger is provided in a plasma discharging technology. Non limiting examples of NTP discharging technology within the scope of the present invention include Glow, corona, an atmospheric pressure plasma jet (APPJ), dielectric barrier discharge (DBD), micro-hollow cathode discharge (MHCD), one atmosphere uniform glow-discharge plasma (OAUGDP), plasma needle, an atmospheric pressure glow discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

Reference is now made to FIG. 7A, illustrating in an out-of-scale-manner a schematic view of an atmospheric pressure plasma jet as an alternative embodiment of the present invention. As been stated by n Nehra et al. (See Nehra V, Kumar A, Dwivedi H (2008) Atmospheric non-thermal plasma sources. *Int J Eng* 2(1):53-68 which is incorporated herein as a reference), discharge capable of generating non-thermal plasmas at atmospheric pressure is atmospheric-pressure plasma jet. This type of APPJ consists of two concentric electrodes through which a mixture of helium, oxygen or other gases flows. In this arrangement, the inner electrode is coupled to 13.56 MHz radio frequency power at a voltage between 100-250 V and the outer electrode is grounded. By applying RF power, the discharge is ignited and operates on a feed stock gas, which flows between an outer grounded, cylindrical electrode and a central electrode and produces a high velocity effluent stream of highly reactive chemical species. Central electrodes driven by radio frequency power accelerate free electrons. These energetic electrons undergo inelastic collisions with the feed gas, producing excited state molecules, atoms, free radicals and additional ion-electron pairs. Once the gas exits the discharge volume, ions and electrons are rapidly lost by recombination, but the fast flowing effluent still contains neutral metastable species and radicals. The key operational features of APPJ are as follows: (1) it produces a stable, homogenous and uniform discharge at atmospheric pressure; (2) operates at radio frequency (RF) power of 250 W and frequency of 13.56 MHz; (3) the ionized gas from the plasma jet exits through the nozzle where it is directed onto the substrate and hence utilized in downstream processing; (4) it operates without a dielectric cover over the electrode, yet is free from filaments, streamers and arcing; (4) The gas temperature of the discharge is as low as 50° C., allowing it to treat delicate surfaces without damage, or as high as 300° C., allowing it to treat robust surfaces much more aggressively. (5) It exhibits a great similarity to low-pressure DC glow discharge.

Reference is now made to FIG. 7B, still illustrating in an out-of-scale-manner a schematic view of a corona discharger (See all details in Nehra et al.) as alternative embodiments of the present invention. Corona discharge technology involves generating non thermal atmospheric plasma. It directly affects the generation of free radicals. Corona discharge exists in several forms, depending on the polarity of the field and the electrode geometrical configuration. Corona discharge arrangements comprising asymmetric electrode pair and results from the electric field that surrounds the inhomogeneous electrode arrangements powered by a continuous or pulsed DC voltage. The development of a coronal discharge preferably involves the following steps: an asymmetric electrode configuration is made; a high voltage is applied and free electric charge is made available; and the creation of electric current multiplication and avalanche breakdown.

In other alternative embodiments involving DBD plasma technology, plasma discharges between two electrodes, at least one electrode insulated with a dielectric layer can be operated in a wide range of geometrical configurations such as the classical volume discharge, surface discharge, and coplanar discharge. Volume discharges can also have either planar or coaxial arrangements. In planar electrode arrangements, the two electrodes are parallel to each other, and one or two dielectric barriers are always located either (i) on the powered or the ground electrode, or (ii) on both the electrodes, or (iii) in between the two metal electrodes. The electrodes in DBD can also be arranged in a coaxial manner having one electrode inside the other with at least one or two dielectric barriers located either (i) on the outer side of the inner electrode/on the inner side of the outer electrode, or (ii) on both the electrodes facing each other, or (iii) in between the two cylindrical electrodes. Besides the volume discharges, other designs also exist that use either surface or coplanar discharge geometry. Surface discharge device have a thin and long electrode on a dielectric surface and an extended counter-electrode on the reverse side of the dielectric. In this configuration, the discharge gap is not clearly defined and so the discharge propagates along the dielectric surface. There also exist combinations of both volume and surface discharge configuration such as the coplanar arrangement used in plasma display panel. The coplanar discharge device is characterized by pairs of long parallel electrodes with opposite polarity, which are embedded within a dielectric bulk nearby a surface. In addition to these configurations, other variants of DBD are also used in various applications. The typical arrangements of DBD, shown by Nehra et al., exhibit two major discharge modes, either filamentary mode, which is the common form of discharge composed of many microdischarges that are randomly distributed over the electrode surface; or homogenous glow discharge mode, also known as atmospheric pressure glow discharge mode due to similarity with dc glow discharges.

Reference is now made to FIG. 8 illustrating in an out-of-scale-manner a schematic view of a system for the administration of a plasma modified field (PMF) to a subject (1000). The system comprising NTP discharger (200) mounted on a plasma modified-field coupling mechanism (PMFCM) comprising dish (10) in a manner that plasma generated by discharger (200) is discharged, influenced or modified or coupled by the field generated by at least one coupling element and optionally, by at least one reflecting element (not shown) fixed on dish (10), and a plasma modified-field (PMF) is discharged (50) in a highly efficient, focused and predefined manner towards object (60).

Figure 9A:
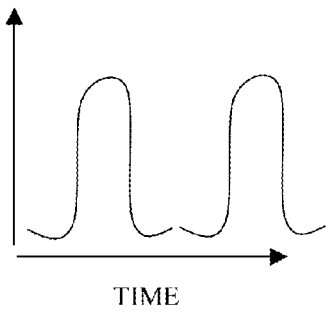
Figure 9B:
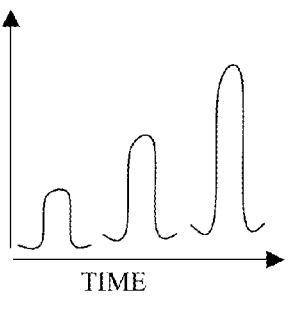
Figure 9C:
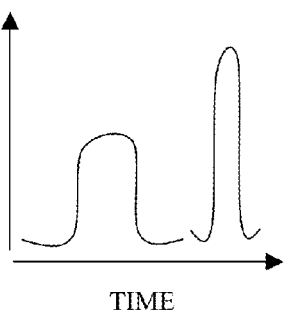
Figure 9D:
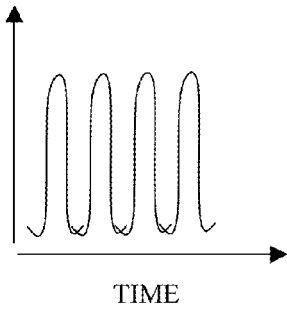
Figure 9E:
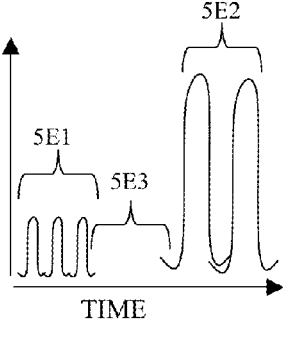
Figure 9F:
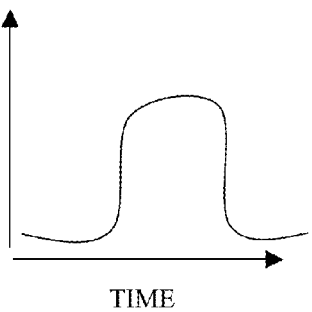

Reference is now made to FIG. 9A-9F illustrating in an out-of-scale-manner a schematic view of plasma modified-field profiles, according to few embodiments of the invention, namely the profile of the intensity of the discharge plasma over time. FIG. 9A illustrates a profile wherein a PMF is discharged in an equal and homogenous intensity over the treatment time. FIG. 9B illustrates a profile wherein PMF is discharged in a non-equal and heterogeneous intensity over the treatment time. Here the intensity of the PMF is increased and the pulse duration is equal along all pulses. Thus, a decrease in intensity and decrease-then-increase and/or increase-then-decrease intensities are possible. FIG. 9C illustrates a profile wherein PMF is discharged non-evenly and in various intensities. FIG. 9D illustrates a profile of many pulses shot in a predefined pattern. FIG. 9E illustrates a profile wherein PMF is discharged non-evenly and in various intensities: at least one first set of pulses (5E1), at least one second set of pulses (5E2), where at least one time laps (e.g., 0 to 1 min., 5E3) is provided between the said two sets of pulses.

In one embodiment, the PMF is applied to the subject in a predetermined mode, particularly pulse series mode, which is determined or more specifically adjusted according to the classification (i.e. taxonomic classification) of the treated subject. For example, a pulse profile designed to induce a regenerative or beneficial effect in a plant may be different (i.e. by pulse duration or pulse intervals or both) from the PMF pulse profile designed to induce a therapeutic or regenerative or beneficial effect in human and/or from the PMF pulse profile designed to induce a beneficial effect on water or gas.

It is in the scope of the invention to disclose a system for the administration of a plasma modified field (PMF) to a subject. The system comprises, inter alio, (a) a non thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. It is within the scope that the first surface of the plasma beam dish is mounted with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing the field. It is also within the scope that the PMFCM and the controller is configured to adjust any of the at least one coupling and reflecting element in a predetermined manner thereby providing the PMF for inducing a therapeutic or regenerative or beneficial effect on the subject.

It is in the scope of the invention wherein the NTP plasma emitting source of the system as defined in any of the above is mounted on the second opposite surface of the plasma beam dish.

It is in the scope of the invention, wherein the controller of the system as defined in any of the above is further adapted to provide pulses of the PMF in a predetermined manner.

It is in the scope of the invention, wherein the NTP emitting source of the system as defined in any of the above is selected from the group consisting of a dielectric barrier discharger, an atmospheric pressure glow discharger, a corona plasma discharger, a high voltage DC corona discharger, a high voltage negative DC corona discharger, a high voltage positive DC corona discharger, a floating electrode dielectric barrier discharger, gliding arc discharge (GD) induced plasma and a plasma jet.

It is in the scope of the invention, wherein the at least one coupling element of the system as defined in any of the above comprises a ferroelectric material characterized by at least one of piezoelectricity, pyroelectricity and memory properties.

It is further within the scope of the invention, wherein the coupling element at least partially comprises Polyvinylidene fluoride, polyvinylidene difluoride (PVDF), PZT, lead zirconium titanate, ferroelectric oxides, $Pb[Zr(x)Ti(1-x)]O_3$, $PbZrO_3$, Barium Titanate ($BaTiO_3$), $(Ba, Sr)TiO_3$, $Ba(1-x)Sr(x)TiO_3$, piezomagnetic ferrite materials, magnetoelectric ceramic materials and any combination thereof.

It is further within the scope of the invention, wherein the coupling element is selected from the group consisting of a permanent magnet, an electromagnet, a superconducting magnet, and any combination thereof.

It is further within the scope of the invention, wherein the ferromagnetic element comprises at least one material selected from the group consisting of Cobalt, Magnetite ($Fe_3O_4$), α-ferrite (α Fe), iron, ferromagnetic alloys and mixtures thereof.

It is further within the scope of the invention, wherein the plasma beam dish, at least partially comprises a polymeric material selected from the group consisting of polycarbonates, Polystyrene (PS), polyesters, polyphenylene oxide, acrylonitrile butadiene styrene (ABS), styrene acrylonitrile, polyimide and blends and polymeric combinations thereof.

It is further within the scope of the invention, wherein the at least one reflecting element at least partially comprises a material or element selected from the group consisting of: high-reflector coating, metals such as iron and alloys thereof, stainless steel, aluminum, silver, gold and mixtures thereof, dielectric coating, extreme ultraviolet coating, high energy UV, glass, amorphous (non-crystalline) solid materials, polymers and any combination thereof.

It is further within the scope of the invention, wherein the at least one plasma beam opening is positioned in the center of the plasma beam dish.

It is further within the scope of the invention, wherein the at least one coupling element is positioned in the center of the plasma beam dish.

It is further within the scope of the invention, wherein the at least one coupling element is arranged radially around the plasma beam opening.

It is further within the scope of the invention, wherein the at least one coupling element is arranged in at least one set of pairs or triplicates or in at least one set of more than three coupling elements.

It is further within the scope of the invention, wherein the PMFCM comprises at least one pair of coupling elements.

It is further within the scope of the invention, wherein the PMFCM comprises at least one pair of oppositely oriented coupling elements.

It is another object of the invention to disclose the system for the administration of a plasma modified field (PMF) as defined above, wherein the PMFCM comprises at least one pair of oppositely oriented pairs of coupling elements.

It is further within the scope of the invention, wherein the at least one pair of coupling elements is arranged in parallel orientation.

It is further within the scope of the invention, wherein the at least one pair of coupling elements is positioned such that the poles of the coupling elements having attractive polarities or repulsive polarities.

It is further within the scope of the invention, wherein the at least one coupling element provides a magnetic field in the range of 25 μT to 10 T and higher.

It is further within the scope of the invention, wherein the at least one coupling element comprises a plurality of coupling elements positioned around the plasma beam opening.

It is further within the scope of the invention, wherein the at least one reflecting element is positioned in the outer rim of the plasma dish.

It is further within the scope of the invention, wherein the at least one reflecting element comprises one, two, three or more reflecting elements, or the at least one reflecting element is configured as a ring-like shape surrounding the plasma beam opening.

It is further within the scope of the invention, wherein the PMF is applied in a pulsed manner or in a continuous manner or in a combination thereof.

It is further within the scope of the invention, wherein the PMF is applied in a series of pulses having predetermined rates and duration.

It is further within the scope of the invention, wherein the PMF is applied in a series of pulses characterized by a constant frequency value.

It is further within the scope of the invention, wherein the PMF is applied in a series of pulses characterized by increasing duration and/or increasing pulse intervals.

It is further within the scope of the invention, wherein the PMF is applied in a series of pulses selected from the group consisting of nanosecond pulses, millisecond pulses, second pulses and a combination thereof.

It is further within the scope of the invention, wherein the PMF is applied at a dose range of between about 0.1 J/cm2 to about 4 J/cm2.

It is further within the scope of the invention, wherein the PMF is applied in a frequency range of between about 100 Hz and about 20 MHz.

It is further within the scope of the invention, wherein the PMF is characterized by a relative dielectric constant in the range of between about 500 and about 2500.

It is further within the scope of the invention, wherein the PMF is characterized by a piezoelectric charge constant in the range of between about 100 (10-12 C/N or 10-12 m/V) to about 1000 (10-12 C/N or 10-12 m/V).

It is further within the scope of the invention, wherein the PMF is characterized by a piezoelectric voltage constant in the range of between about 5 (10-3 Vm/N or 10-3 m2/C) to about 50 (10-3 Vm/N or 10-3 m2/C).

It is further within the scope of the invention, wherein the PMF is characterized by frequency constants in the range of between about 1000 (Hz.m or m/s) to about 5000 (Hz.m or m/s).

It is further within the scope of the invention, wherein the power of a pulse of the potential (or voltage) ranges between about 0.1 W to about 10 W.

It is in the scope of the invention wherein the system as defined in any of the above is provided useful for treating, objects, human, animals, plant and fluids, such as water, milk and blood, other media, gas and liquid and gas mixtures.

It is in the scope of the invention wherein the system as defined in any of the above is provided useful for functional recovery, for pain relief, water purification, gas pollution purification, ozone decomposition, disease and/or medical disorders therapy, plant growth, increase and improve agriculture yield, such as fruit size, fruit weight and increase root system strength.

It is further within the scope of the invention, wherein said subject is selected from the group consisting of: human, animal, plant, flatworms, planaria, fluids, soil, minerals, media, gas, liquid and gas mixtures and any predetermined object.

It is further within the scope of the invention, wherein the system is adapted to provide a therapeutic or regenerative or beneficial effect on cells, tissues, tissue culture, organs and a combination thereof.

It is further within the scope of the invention, wherein the system is adapted to provide an effect beneath the outer integument of the treated subject.

It is further within the scope of the invention, wherein the system is adapted to provide a synergic effect with respect to inducing a therapeutic or regenerative or beneficial effect on the subject as compared to the effect induced by each of the plasma coupled elements individually administered.

It is further within the scope of the invention, wherein the applied PMF affect the brain.

It is further within the scope of the invention, wherein the applied PMF is adapted to affect at least one brain cell or tissue type selected from the group consisting of: neurons, nerve cells, glial cells, brain membranes, the frontal brain lobe, the parietal brain lobe, the occipital brain lobe, the temporal brain lobe, the cortex, cranium, basal ganglia, brain stem, cerebellum, dura, the spinal cord and any combination thereof.

It is further within the scope of the invention, wherein the PMF discharge effect provided by the system of the present invention can be detected by detecting means and methods including among other direct measures such as gas discharge visualization (GDV) means, Kirlian photography means, digital visualization of biofield (DVB) and indirect measurement such as a superconducting quantum interference device (SQUID), biophton measurement, Biophoton Imaging, CCD (charge-coupled device), photomultiplier tube (PT), eletrophotonic imaging or Electro Photon Imaging (EPI).

It is further within the scope of the invention, wherein said applied PMF is adapted to affect biochemical parameters selected from the group consisting of: brain related parameters, protein fingerprint or profile, enzymatic activity, protein crystallization, medical therapeutic effects, improved plant parameters, improved water parameters, improved air pollution parameters, gas parameters, treatment of gaseous emissions, ozone treatment, increased functional recovery after a disruptive effect, improved immune system, skin related parameters, wound healing, recovery from bacterial infection, recovery from viral infection, tissue regeneration, pain relief, antioxidant activity, improved rheological properties and any combination thereof.

It is further within the scope of the invention, wherein said system is adapted to induce a therapeutic effect on a disease or condition selected from the group consisting of: rheological properties of blood, autoimmune diseases, degenerative diseases, neurological diseases, neurodegenerative diseases, inflammatory diseases, cancer-related diseases, cardiovascular diseases, skin-related diseases or conditions, pain relief, antiaging, functional recovery after having a disruptive effect, bowel-related diseases, enteric diseases, attention disorder (ADHD) syndromes and any combination thereof.

It is further within the scope of the invention, wherein said skin-related diseases or conditions are selected from the group consisting of: wound, burn injury, fresh trauma wound, skin infections, skin injuries such as scratches or scraps, skin inflammatory disease, psoriasis, dermatitis, lupus, necrosis, gangrene, eczema, atopic dermatitis, chronic wounds, skin cells regeneration, wrinkles, acne, UV radiation diseases, skin cancer, malignancy, cancerous tissue, melanoma, nodular melanoma, Acral lentiginous melanoma, Lentigo maligna, Superficial spreading melanoma, basal cell carcinoma, Bowen's disease, infections wounds, ulcers, burn injuries, fresh trauma wounds, wound at a haemostasis stage, wound at an inflammation stage, wound at a granulation or proliferation stage, wound at a contracture stage, wound at an epithelisation stage, wound at cancerous stage and any combination thereof.

According to certain embodiments, it is herein acknowledged that basal-cell carcinomas may include the following types: Nodular basal-cell carcinoma (Classic basal-cell carcinoma), Cystic basal-cell carcinoma, Cicatricial basal-cell carcinoma (Morpheaform basal-cell carcinoma, Morphoeic basal-cell carcinoma), Infiltrative basal-cell carcinoma, Micronodular basal-cell carcinoma, Superficial basal-cell carcinoma (Superficial multicentric basal-cell carcinoma), Pigmented basal-cell carcinoma, Rodent ulcer (Jacobi ulcer), Fibroepithelioma of Pinkus, Polypoid basal-cell carcinoma, Pore-like basal-cell carcinoma and Aberrant basal-cell carcinoma.

In other certain embodiments, basal-cell carcinoma may be divided into 3 groups, based on location and difficulty of therapy: (1) Superficial basal-cell carcinoma, which is considered as equivalent to "in-situ". Up until the present invention it is known to be effectively treated with topical chemotherapy; (2) Infiltrative basal-cell carcinoma, which often encompasses morpheaform and micronodular basal-cell cancer. Up until the present invention it is known as being more difficult to treat with conservative treatment methods such as electrodessiccation and curettage, or with curettage alone; and (3) Nodular basal-cell carcinoma, which essentially includes most of the remaining categories of basal-cell cancer. It is well within the scope of the present invention that it is not unusual to encounter morphologic features of several variants of basal-cell cancer in the same tumor. It is also within the scope of the present invention that Nevoid basal-cell carcinoma syndrome is treated by the system of the present invention.

According to a further embodiment, Melanoma include three categories that begin in situ, meaning they occupy only the top layers of the skin, and may become invasive; the fourth category is invasive from the start. It is herein acknowledged that invasive melanomas are more severe, as they have penetrated deeper into the skin and may have spread to other areas of the body. It is also within the scope of the invention that superficial spreading melanoma is the most common type. This melanoma grows along the top layer of the skin for a relatively long period of time before penetrating more deeply. This type of melanoma can occur in a previously benign mole. The melanoma can be found almost anywhere on the body.

Reference is now made to Lentigo maligna which is similar to the superficial spreading type, as it also remains close to the skin surfacein the first stage of the disease, and usually appears as a flat or mildly elevated mottled tan, brown or dark brown discoloration. When this cancer becomes invasive, it is referred to as lentigo maligna melanoma.

Reference is now made to Acral lentiginous melanoma, also spreads superficially before penetrating more deeply. This type of melanoma can often advance more quickly than superficial spreading melanoma and lentigo maligna.

Reference is now made to Nodular melanoma, which is usually invasive at the time it is first diagnosed. The malignancy is recognized when it becomes a bump. The most frequent locations are the trunk, legs, and arms, mainly of elderly people, as well as the scalp in men. This is the most aggressive of the melanomas, and is found in 10 to 15 percent of cases.

Reference is now made to Bowen's disease, also related to as intraepidermal carcinoma, IEC or Squamous cell carcinoma in-situ.

It is further within the scope of the invention, wherein said degenerative diseases or neurological diseases or neurodegenerative diseases or disorders thereof are selected from the group consisting of: Parkinson, Alzheimer, Huntington, Alzheimer, Amyotrophic lateral sclerosis (ALS), Friedreich's ataxia, Lewy body disease, Spinal muscular atrophy, Creutzfeldt-Jakob disease, Primary progressive aphasia (PPA), Progressive supranuclear palsy (PSP) (or the Steele-Richardson-Olszewski syndrome), Multiple system atrophy, Multiple sclerosis, Niemann Pick disease, Atherosclerosis, Cancer, Essential tremor, Tay-Sachs Disease, Diabetes, Heart Disease, Keratoconus, Keratoglobus, Inflammatory Bowel Disease (IBD), Prostatitis, Osteoarthritis, Osteoporosis, Rheumatoid Arthritis, Chronic traumatic encephalopathy, Chronic Obstructive Pulmonary Disease (COPD) and Marfan's Syndrome.

It is further within the scope of the invention, wherein said plant parameters are selected from the group consisting of plant vigor, plant growth, fruit size, fruit yield, improved root system, stress tolerance, stem height, seed germination and any combination thereof.

It is further within the scope of the invention, wherein said improved water parameters are selected from the group consisting of: oxidation effect, induction of degradation of organic compounds, water purification, destruction of pathogens such as bacteria and viruses, clearing radioactive isotopes and heavy metals, sterilization, pH values, hydrogen peroxide values, water disinfection, water contamination parameters, effect on mineral ions such as calcium and magnesium, oxidation of inorganic ions and any combination thereof.

It is further within the scope of the invention, wherein the protein fingerprint or profile is associated with a cellular pathway or a protein family selected from the group consisting of signal transduction, stress response, cell cycle, antioxidation, DNA repair, replication, blood plasma proteins, glycoproteins, lypoproteins and any combination thereof.

It is further within the scope of the invention, wherein the protein fingerprint or profile is associated with a protein member selected from a group consisting of Transferin, Serum Amyloid A, XPA, PKB, IMP, MMR, XPA, hTLRs, NE, Transthyretin, LRR, Ku, NLR, catalase, superoxide dismutase, peroxidases, PAT, LTP, Apm1, NLR, LPAF, beta glucanses, Ferredoxin and any combination thereof.

It is further within the scope of the invention, wherein the plant parameters are selected from the group consisting of plant vigor, plant growth, fruit size, fruit yield, improved root system, stress tolerance, stem height, seed germination and any combination thereof.

It is further within the scope of the invention, wherein the improved fluid or gas parameters are selected from the group consisting of: oxidation effect, induction of degradation of organic compounds, water or gas purification, destruction of pathogens such as bacteria and viruses, clearing radioactive isotopes and heavy metals, removal of hazardous substances, removal of SO2, sterilization, pH values, hydrogen peroxide values, water or gas disinfection, water or gas contamination parameters, effect on mineral ions such as calcium and magnesium, oxidation of inorganic ions and any combination thereof.

It is further within the scope of the invention, wherein the system is adapted to provide an effect in vivo and/or in vitro.

It is further within the scope of the invention to disclose a method for generating a plasma modified field (PMF), comprising steps of: (a) emitting non thermal plasma (NTP) beam from a plasma emitting source; (b) providing a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core embodiment, the method further comprises a step of mounting the first surface of the plasma beam dish with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field. It is within the scope the method further comprises a step of configuring the PMFCM and the controller to adjust any of the at least one coupling and reflecting element in a predetermined manner thereby generating the PMF.

It is further within the scope of the invention to disclose a method for inducing a therapeutic or regenerative or beneficial effect on a subject comprising the steps of: (a) providing a system for the administration of a plasma modified field (PMF) to a subject as defined above; and (b) applying the PMF to the subject in a predetermined manner. In this way the PMFCM and the controller are configured to adjust any of the at least one coupling and reflecting element in a predetermined manner thereby providing the PMF for inducing a therapeutic or regenerative or beneficial effect on the subject.

It is further within the scope of the invention to disclose the use of the system for the administration of a plasma modified field (PMF) to a subject. The use comprising steps of providing a system with: (a) a non thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core embodiment, the use further comprises a step of mounting the first surface of the plasma beam dish with: (i) at least one coupling element; and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field. It is within the scope that the use further comprises a step of configuring the PMFCM and the controller to adjust any of the coupling and reflecting element in a predetermined manner thereby providing the PMF for inducing a therapeutic or regenerative or beneficial effect on the subject.

It is further within the scope of the invention to disclose a method of manufacturing a system for the administration of a plasma modified field (PMF) to a subject comprising steps of assembling a system by steps of providing: (a) a non thermal plasma (NTP) emitting source for emitting a plasma beam; (b) a plasma modified field coupling mechanism (PMFCM) comprising a plasma beam dish having at least one opening for the passage of the plasma beam; the plasma beam dish having a first surface and a second opposite surface; and (c) a controller for controlling the PMFCM. In a core aspect, the method comprises an additional step of mounting the first surface of the plasma beam dish with: (i) at least one coupling element, and (ii) at least one reflecting element. The at least one coupling element is selected from the group consisting of: (1) at least one ferroelectric element for providing the field; (2) at least one ferromagnetic element for providing the field; (3) at least one piezoelectric element for providing the field and (4) at least one piezomagnetic element for providing said field. It is within the scope that the method comprises an additional step of configuring the PMFCM and the controller to adjust any of the coupling and reflecting element in a predetermined manner thereby providing the PMF for inducing a therapeutic or regenerative or beneficial effect on the subject.

In order to understand the invention and to see how it may be implemented in practice, a plurality of preferred embodiments will now be described, by way of non-limiting example only, with reference to the following examples.

EXAMPLE 1

Effect of the System for the Administration of a Plasma Modified Field on Water Parameters and Water Purification The effect of PMF treatment, using the system of the present invention, is herein assessed with reference to improvement of water parameters. It is within the scope of the present invention that the system and method for the administration of PMF is used for providing beneficial effects on fluids and specifically on water.

An exemplary system demonstrates an effect on water chemistry parameters. In this embodiment, an apparatus for the administration of plasma modified field (i.e. generated by magnetic and/or electric fields) such as a pulsed ferroelectric corona, testes the effect of discharged PMF on water chemistry, i.e. water pH and $H_2O_2$ concentration. A pulsed high voltage power supply is connectable to a coupling mechanism or positionable reactor (i.e. PMFCM). The power supply is connected via HV electrode. The PMFCM reactor is mounted with a ferroelectric disk as a coupling element. The ferroelectric disk preferably characterized as follows: it has a diameter Ø of about 1 to 2.25 cm, it made of piezoelectric material such as APC 841 as described below in Table 1. In specific embodiments, the electrode gap is between 4 to 8 mm, the Voltage ranges between about 20 to 35 kV and the duration ranges from 10 to 22 nanoseconds.

According to certain embodiments, the system as generally illustrated above is characterized by the properties as described in Table 1.

Reference is now made to Table 1, describing physical and piezoelectric properties of APC materials, available by http://www.americanpiezo.com/apc-materials/piezoelectric-properties.html.

TABLE 1

Selected properties of certain embodiments of the system of the present invention

| APC Material: | 840 | 841 | 850 | 855 | 880 |
|---|---|---|---|---|---|
| Navy Type Equivalent | Navy I | — | Navy II | Navy VI | Navy III |
| Relative Dielectric Constant | | | | | |
| $K^T$ | 1250 | 1350 | 1900 | 3300 | 1000 |
| Dielectric Dissipation Factor (Dielectric Loss(%))* | | | | | |
| tan δ | 0.40 | 0.35 | 1.40 | 1.30 | 0.35 |
| Curie Point (° C.)** | | | | | |
| $T_c$ | 325 | 320 | 360 | 250 | 310 |
| Electromechanical Coupling Factor | | | | | |
| $k_p$ | 0.59 | 0.60 | 0.63 | 0.68 | 0.50 |
| $k_{33}$ | 0.72 | 0.68 | 0.72 | 0.76 | 0.62 |
| $k_{31}$ | 0.35 | 0.33 | 0.36 | 0.40 | 0.30 |
| $k_{15}$ | 0.70 | 0.67 | 0.68 | 0.66 | 0.55 |
| Piezoelectric Charge Constant ($10^{-12}$ C/N or $10^{-12}$ m/V) | | | | | |
| $d_{33}$ | 290 | 300 | 400 | 630 | 215 |
| $-d_{31}$ | 125 | 109 | 175 | 276 | 95 |
| $d_{15}$ | 480 | 450 | 590 | 720 | 330 |
| Piezoelectric Voltage Constant ($10^{-3}$ Vm/N or $10^{-3}$ m²/C) | | | | | |
| $g_{33}$ | 26.5 | 25.5 | 24.8 | 21.0 | 25.0 |
| $-g_{31}$ | 11.0 | 10.5 | 12.4 | 9.0 | 10.0 |
| $g_{15}$ | 38.0 | 35.0 | 36.0 | 27.0 | 28.0 |
| Young's Modulus ($10^{10}$ N/m²) | | | | | |
| $Y^E_{11}$ | 8.0 | 7.6 | 6.3 | 5.9 | 9.0 |
| $Y^E_{33}$ | 6.8 | 6.3 | 5.4 | 5.1 | 7.2 |
| Frequency Constants (Hz*m or m/s) | | | | | |
| $N_L$ (longitudinal) | 1524 | 1700 | 1500 | 1390 | 1725 |
| $N_T$ (thickness) | 2005 | 2005 | 2040 | 2079 | 2110 |
| $N_P$ (planar) | 2130 | 2055 | 2080 | 1920 | 2120 |
| Density (g/cm³) | | | | | |
| ρ | 7.6 | 7.6 | 7.6 | 7.7 | 7.6 |
| Mechanical Quality Factor | | | | | |
| $Q_m$ | 500 | 1400 | 80 | 65 | 1000 |

According to specific embodiments, this example relates to properties of a system comprising a ferroelectric material APC841.

It is within the scope of the invention that the system of the present invention is configured to provide enhanced properties, i.e. improved in at least 5% relative to the properties presented in Table 1.

It is further within the scope that plasma modified field is discharged to affect water sample. In this experiment in a pre-calibrated system, a sample containing 200 μl distilled water disposes at a distance of about 2 mm from the PMFCM reactor. In this case, the effect on pH and $H_2O_2$ indicates that hydrogen peroxide pre-calibrated test strips can be used, e.g., EM Quant colorimetric test strips, with the range of 1-100 mg/L. By (1) dipping the strips into a sample, (2) waiting for color to stabilize and (3) matching color visually to color range provided, an effect can be observed after a few (10-20) second of treatment. $H_2O_2$ accumulates in a rapid rate, increases dramatically in a rate of about 10 mg/L after about 60 seconds of treatment.

A pre-calibrated pH meter proves the effect on pH values may in a method which includes following of (1) dipping the electrode into the sample and (3) waiting for pH to stabilize. The method proves that a decrease in water pH values along the initial period of time (about 40 to 60 seconds of treatment). pH values decreases from about 6 to about 4 and less.

Thus it is herein shown that exposing water to PMF emitted by the system of the present invention results in significantly affecting water parameters. It is emphasized that the effect is made without introducing any chemical or biological material or object to the water or fluid. In other embodiments, the system of the present invention may be used to cause cleaning affects of the treated water as compared to a control sample. The cleaning affect may be established by parameters associated with water or any other fluid or gas quality or purification of contamination. These parameters may be chemical, physical and biological characteristics of water or any other fluid or gas.

It is herein acknowledged that the water quality characteristics are frequently used by reference to a set of standards against which compliance can be assessed. The most common standards used to assess water quality relate to health of ecosystems, safety of human contact and drinking water. Different uses raise different concerns and therefore different standards are considered. The system and method for administration of plasma modified field (PMF) is used in a non limiting manner for water or any other fluid or gas purification, disinfection, cleaning of heavy metals or pollution. Other parameters which can be affected by exposure to the PMF treatment as disclosed hereinabove include in a non limiting manner pH, dissolved oxygen, oxygen peroxide, conductivity, oxygen reduction potential (ORP) and turbidity. These affects can be achieved, for example, by the following procedure;

Plasma is delivered from a plasma emitter, i.e. a device as illustrated in FIG. 7A or 7B. A plasma modified-field (PMF) is generated and applied to the tested subjects using the plasma modified-field coupling mechanism (PMFCM) of the present invention, i.e. as illustrated in FIG. 1.

According to certain aspects of the invention, PMF is discharged in a series of pulses, i.e. as described in FIG. 9. According to one option a set of PMF pulses is provided having increasing pulse duration in the range of 1 sec and 5 sec and increasing time laps between the pulses in the range of 1 min to 5 min.

To conclude, it is submitted that the plasma modified field (PMF) system, i.e. as shown in FIGS. 1 and 2 and treatment protocols as disclosed above, is configured to provide a therapeutic or regenerative or beneficial effect on water as well as on human, animal and plants.

EXAMPLE 2

The Effect of the System for the Administration of Plasma Modified Field on Inducing a Regenerative Result on Human In order to demonstrate the therapeutic effect of plasma modified field (PMF) treatment on human and animals using the gas plasma signal device of the present invention, the following experiment is set out.

The effect of the PMF generating device of the present invention is tested on the protein profile of treated as compared to untreated control subjects. A further control made was profiling predetermined proteins before and after treatment with the system of the present invention. The protein profile of blood samples derived from treated subjects applied with the plasma pulses protocol herein disclosed is compared with the protein profile of the control subjects. Plasma is delivered from a plasma emitter, i.e. a device as illustrated in FIGS. 7A-B, in other embodiments, by a magnetic blow-out glidarc reactor. A plasma modified-field (PMF) is generated and applied to the tested subjects using the coupling mechanism (PMFCM) of the present invention, i.e. as illustrated in FIG. 1 or FIG. 2.

According to certain aspects of the invention, PMF is discharged in a series of pulses, i.e. as described in FIG. 9.

The effect of the PMF treatment as described above, on protein regeneration, is tested in vivo by analyzing the protein profile or fingerprint in blood samples obtained before and after the treatment. Examples of proteins which may be affected by the PMF treatment include proteins associated with signal transduction, proteins associated with stress response, proteins involved in cell cycle, antioxidant related proteins and enzymes, nuclear proteins associated with DNA repair, replication factors, blood plasma proteins, glycoproteins, lypoproteins and combinations thereof. More specific examples of proteins affected by the herein disclosed NTP provided with an electromagnetic field treatment include a protein member selected from a group consisting of Transferin, Serum Amyloid A, XPA, PKB, IMP, MMR, XPA, hTLRs, NE, Transthyretin, LRR, Ku, NLR, catalase, superoxide dismutase, peroxidases and any combination thereof.

EXAMPLE 3

The Effect of the System for the Administration of a Plasma Modified Field of the Present Invention on Inducing a Functional Recovery Result on Animals and Plants In order to demonstrate the effect of the PMF treatment as disclosed inter alia, on the recovery from a disruptive effect such a physical or mental disease or condition in animals and human or a stress condition in plants, the following experiment is performed.

The effect of pretreatment with the PMFCM of the present invention is tested on the functional recovery after a disruptive effect. The protein profile of pretreated subjects is compared to control subjects having the same disruptive effect but not exposed to PMF pretreatment with the gas plasma signal reactor of the present invention. The protein profile of samples derived from pretreated subjects applied with the PMF pulses protocol herein disclosed is compared with the protein profile of the control subjects. Furthermore, the protein profile of treated subjects is compared to their profile before treatment. The PMF pretreatment may be provided by the following procedure. Plasma is delivered from a plasma emitter, i.e. a device as illustrated in FIGS. 7A-B. A plasma modified field (PMF) is generated and applied to the tested subjects using the plasma modified field coupling mechanism (PMFCM) of the present invention, i.e. as illustrated in FIG. 1 or 2.

According to certain aspects of the invention, PMF is discharged in a series of pulses, i.e. as described in FIG. 9.

The effect of the PMF pretreatment as described above, on functional recovery, can be tested in vivo by analyzing the protein profile or fingerprint of samples obtained from the treated subjects as compared to the control subjects and/or as compared to the protein profile of the subjects before treatment. The functional recovery rate may be tested by analyzing predetermined protein candidates or biological or chemical markers at increasing time intervals from the disruptive effect. A faster recovery curve is observed in the treated subjects as compared to the control subjects. Examples of proteins which may be affected by the PMF treatment include proteins associated with signal transduction, proteins associated with stress response, proteins involved in cell cycle, nuclear proteins associated with DNA repair, replication factors, blood plasma proteins, glycoproteins, lypoproteins and combinations thereof. More specific examples of proteins affected by the herein disclosed NTP treatment include a protein member selected from a group consisting of Transferrin, Serum Amyloid A, XPA, PKB, IMP, MMR, XPA, hTLRs, NE, Transthyretin, LRR, Ku, NLR, catalase, superoxide dismutase, peroxidases and any combination thereof.

EXAMPLE 4

The Effect of the System for the Administration of a Plasma Modified Field on Plants In order to demonstrate the effect of PMF treatment using the system of the present invention on plants, the following experiment is performed.

The effect of the plasma coupling system of the present invention is tested on plants exposed to the PMF as disclosed hereinabove, in comparison to untreated control plants.

Non thermal plasma is delivered from a plasma emitter, i.e. a device as illustrated in FIGS. 7A-B. A plasma modified field (PMF) is generated and applied to the tested subjects using the plasma modified field coupling mechanism (PMFCM) of the present invention, i.e. as illustrated in FIG. 1 or 2.

According to certain aspects of the invention, PMF is discharged in a series of pulses, i.e. as described in FIG. 9.

The effect of the PMF treatment as described above is tested on various beneficial crops, particularly on the root of the plant. The regenerative effect of the treatment can be demonstrated by evaluating parameters associated with improved plant growth, improved plant yield and improved resistance to biotic and abiotic stresses. Such parameters include in a non limiting manner, plant growth rate, plant height, fruit yield, fruit size, improved and extended root system, fruit brix and combinations thereof. By using the system of the present invention improvement of at least one parameter associated with plant growth and plant yield is measured in plants exposed to the PMF, as compared to untreated control plants grown in the same conditions. Non limiting examples of candidate proteins affected by exposure of the plant (i.e. root) to PMF may include at least one of: PAT LTP, LRR, Apm1, NLR, LPAF, beta glucans and Ferredoxin.

EXAMPLE 5

Equations Describing the Generated Plasma Modified Field

The plasma potential or the space potential is herein defined as the magnitude of the generated potentials and electric fields as described by the following parameters:

$\xi$ denotes a parameter defining the plasma field, i.e. plasma displacement vector, it is herein calculated by the following equation:

$\xi = (n \cdot r_D^3)^{-1}$, where;

n is the number of charged particles; and
rD is the Debye length (also called Debye radius).

$K' = \xi \cdot m'$, where;

m' is the modified plasma mass

In the case wherein the plasma is coupled to or generated by one type of coupling element:

Reference is now made to the energy of plasma modified by one coupling element that may be selected from the group consisting of: at least one piezoelectric element, at least one ferromagnetic element, at least one ferroelectric means and at least one piezomagnetic means, described by the following equation:

$$\varepsilon = \frac{3\pi^5 (K' \cdot T)^2}{\alpha},$$

where;
T is the temperature (also temperature per time unit); and
$\alpha$ is the field frequency of the treated subject or object.

In the case wherein the plasma is coupled to or generated by a combination of two types of coupling elements:

Reference is now made to the energy of plasma modified by two types of coupling elements selected from the group consisting of any combination of two elements selected from the group consisting of: at least one piezoelectric element, at least one ferromagnetic element, at least one ferroelectric element and at least one piezomagnetic element.

as described by the following equation:

$$\varepsilon = \frac{3\pi^5 (K' \cdot T)^3}{\alpha},$$

where;
T is the temperature (also temperature per time unit); and
$\alpha$ is the field frequency of the treated subject or object.

Equations describing the energy resulting from the interaction between the generated plasma and the treated object The reactive energy generated by plasma modified by at least one of a piezoelectric means, a ferroelectric means, ferromagnetic means and piezomagnetic means can be described by the following equations:

$$\frac{\varepsilon}{\alpha} = m \cdot c$$

$$\varepsilon = m \cdot c \cdot \alpha,$$

where;
m is the energy mass discharged (plasma along with the coupled element/s);
c is the speed of light in a vacuum; and
$\alpha$ is the field frequency of the treated subject or object.

It is also within the scope of the invention that the energy characterizing the plasma modified by one type of coupling element, preferably selected from the group consisting of a piezoelectric means, a ferroelectric means, ferromagnetic means and piezomagnetic means is equal to the reactive energy of the object resulting from the PMF energy. This can be described by the following equation:

$$\frac{3\pi^5 (K' \cdot T)^2}{\alpha} = m \cdot c \cdot \alpha$$

It is also within the scope of the invention that the energy characterizing the plasma modified by any combination of two coupling elements selected from the group consisting of a piezoelectric means, a ferroelectric means, ferromagnetic means and a piezomagnetic means is equal to the reactive energy of the object resulting from the PMF energy. This can be described by the following equation:

$$\frac{3\pi^5 (K' \cdot T)^3}{\alpha} = m \cdot c \cdot \alpha$$

The invention claimed is:

1. A system for generating modified plasma, said system comprising:
   a. a nonthermal plasma (NTP) emitting source for emitting a plasma beam; and
   b. a plasma coupling mechanism (PCM), wherein said PCM comprises a plasma beam dish having at least one opening for the passage of said plasma beam; said plasma beam dish having a first surface and a second opposite surface; said first surface of said plasma beam dish is mounted with at least one coupling element selected from a group consisting of:
      1. at least one ferroelectric element for providing a ferroelectric induced field for coupling with said plasma beam; and
      2. at least one ferromagnetic element for providing a ferromagnetic induced field for coupling with said plasma beam;

further wherein said system additionally comprises at least one reflecting element configured to focus said plasma beam, thereby providing said modified plasma.

2. A method for generating modified plasma, said method comprises steps of:
   a. emitting a non thermal plasma (NTP) beam from a plasma emitting source; and
   b. providing a plasma coupling mechanism (PCM) wherein said PCM comprises a plasma beam dish having at least one opening for passage of said NTP plasma beam; said plasma beam dish having a first surface and a second opposite surface; and mounting said first surface of said plasma beam dish with at least one coupling element selected from the group consisting of:
      1. at least one ferroelectric element for providing a ferroelectric induced field for coupling with said NTP plasma beam; and
      2. at least one ferromagnetic element for providing a ferromagnetic induced field for coupling with said NTP plasma beam;

further wherein said method additionally comprises a step of mounting said PCM further comprising at least one reflecting element configured to focus said NTP plasma beam thereby generating said modified plasma.

* * * * *